US012036099B2

(12) United States Patent
Schneider et al.

(10) Patent No.: US 12,036,099 B2
(45) Date of Patent: *Jul. 16, 2024

(54) METHODS AND APPARATUSES FOR MAKING ELASTOMERIC LAMINATES WITH ELASTIC STRANDS UNWOUND FROM SPOOLS ON SURFACE UNWINDERS

(71) Applicant: The Procter & Gamble Company, Cincinnati, OH (US)

(72) Inventors: Uwe Schneider, Cincinnati, OH (US); Joseph Allen Eckstein, Sunman, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/734,407

(22) Filed: May 2, 2022

(65) Prior Publication Data

US 2022/0257427 A1 Aug. 18, 2022

Related U.S. Application Data

(63) Continuation of application No. 17/191,772, filed on Mar. 4, 2021, now Pat. No. 11,344,453, which is a
(Continued)

(51) Int. Cl.
*A61F 13/15* (2006.01)
*A61F 13/49* (2006.01)
(Continued)

(52) U.S. Cl.
CPC .... *A61F 13/15593* (2013.01); *A61F 13/4902* (2013.01); *A61F 13/49061* (2013.01);
(Continued)

(58) Field of Classification Search
CPC .............. D04H 3/12; B32B 2555/02; B32B 2307/726; B32B 2307/51; B32B 2305/20;
(Continued)

(56) References Cited

U.S. PATENT DOCUMENTS 3,113,225 A  12/1963  Claus
3,434,189 A   3/1969  Buck et al.
(Continued)

FOREIGN PATENT DOCUMENTS

CA  2158790 A1  3/1996
CN  1461634 A  12/2003
(Continued)

OTHER PUBLICATIONS

15040 PCT International Search Report, PCT/US2017/067251, dated Jun. 14, 2018, 13 pages.
(Continued)

*Primary Examiner* — Vishal I Patel
(74) *Attorney, Agent, or Firm* — Charles R. Matson

(57) ABSTRACT

The present disclosure relates to methods for assembling elastomeric laminates, wherein elastic material may be stretched and joined with either or both first and second substrates. First spools are rotated to unwind first elastic strands from a first unwinder in a machine direction. The first elastic strands are positioned between the first substrate and the second substrate to form an elastomeric laminate. Before the first elastic strands are completely unwound from the rotating first spools, second spools are rotated to unwind second elastic strands from a second unwinder. Subsequently, the advancement of the first elastic strands from the first unwinder is discontinued. Thus, the elastomeric laminate assembly process may continue uninterrupted while switching from an initially utilized elastic material drawn
(Continued)

from the first spools to a subsequently utilized elastic material drawn from the second spools.

8 Claims, 25 Drawing Sheets

Related U.S. Application Data continuation of application No. 15/846,382, filed on Dec. 19, 2017, now Pat. No. 10,966,873.

(60) Provisional application No. 62/581,278, filed on Nov. 3, 2017, provisional application No. 62/553,149, filed on Sep. 1, 2017, provisional application No. 62/553,171, filed on Sep. 1, 2017, provisional application No. 62/553,538, filed on Sep. 1, 2017, provisional application No. 62/483,965, filed on Apr. 11, 2017, provisional application No. 62/436,589, filed on Dec. 20, 2016.

(51) Int. Cl.

| | |
|---|---|
| *A61F 13/513* | (2006.01) |
| *A61F 13/53* | (2006.01) |
| *A61F 13/56* | (2006.01) |
| *A61F 13/64* | (2006.01) |
| *A61F 13/84* | (2006.01) |
| *B05C 1/08* | (2006.01) |
| *B29C 65/00* | (2006.01) |
| *B29C 65/08* | (2006.01) |
| *B29C 65/48* | (2006.01) |
| *B29C 65/74* | (2006.01) |
| *B29K 701/12* | (2006.01) |
| *B29L 31/48* | (2006.01) |
| *B32B 5/04* | (2006.01) |
| *B32B 27/12* | (2006.01) |
| *B32B 37/00* | (2006.01) |
| *B32B 37/12* | (2006.01) |
| *B32B 37/14* | (2006.01) |
| *B32B 37/22* | (2006.01) |
| *B65H 39/16* | (2006.01) |
| *B65H 51/30* | (2006.01) |
| *D01D 5/08* | (2006.01) |
| *D01F 6/04* | (2006.01) |
| *D04H 3/12* | (2006.01) |

(52) U.S. Cl.
CPC ............ *A61F 2013/15292* (2013.01); *A61F 2013/15373* (2013.01); *A61F 2013/15406* (2013.01); *A61F 2013/15447* (2013.01); *A61F 2013/1552* (2013.01); *A61F 2013/15552* (2013.01); *A61F 13/15601* (2013.01); *A61F 13/15699* (2013.01); *A61F 13/15739* (2013.01); *A61F 13/15764* (2013.01); *A61F 2013/15869* (2013.01); *A61F 2013/1591* (2013.01); *A61F 2013/15918* (2013.01); *A61F 2013/15959* (2013.01); *A61F 13/49012* (2013.01); *A61F 13/49015* (2013.01); *A61F 13/49017* (2013.01); *A61F 13/49019* (2013.01); *A61F 2013/49022* (2013.01); *A61F 2013/49025* (2013.01); *A61F 2013/49026* (2013.01); *A61F 2013/49074* (2013.01); *A61F 2013/49092* (2013.01); *A61F 2013/49093* (2013.01); *A61F 2013/51322* (2013.01); *A61F 13/53* (2013.01); *A61F 2013/530343* (2013.01); *A61F 2013/53043* (2013.01); *A61F 13/5622* (2013.01); *A61F 13/64* (2013.01); *A61F 2013/8497* (2013.01); *B05C 1/0808* (2013.01); *B29C 65/08* (2013.01); *B29C 65/086* (2013.01); *B29C 65/48* (2013.01); *B29C 65/74* (2013.01); *B29C 66/00* (2013.01); *B29C 66/344* (2013.01); *B29C 66/8141* (2013.01); *B29C 66/83411* (2013.01); *B29K 2701/12* (2013.01); *B29K 2995/0046* (2013.01); *B29L 2031/4878* (2013.01); *B32B 5/04* (2013.01); *B32B 27/12* (2013.01); *B32B 37/0053* (2013.01); *B32B 37/12* (2013.01); *B32B 37/144* (2013.01); *B32B 37/22* (2013.01); *B32B 2305/20* (2013.01); *B32B 2307/51* (2013.01); *B32B 2307/726* (2013.01); *B32B 2555/02* (2013.01); *B65H 39/16* (2013.01); *B65H 51/30* (2013.01); *C08J 2300/26* (2013.01); *D01D 5/08* (2013.01); *D01F 6/04* (2013.01); *D04H 3/12* (2013.01)

(58) Field of Classification Search
CPC ....... B32B 37/12; B32B 37/0053; B32B 5/04; A61F 2013/15373; A61F 2013/15292; A61F 13/64; A61F 13/5622; A61F 13/53; A61F 13/49019; A61F 13/49017; A61F 13/49015; A61F 13/49012; A61F 13/15764; A61F 13/15739; A61F 13/15699; A61F 13/15601; A61F 13/4902; A61F 13/15593

See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A | 4/1971 | Hansen |
| 3,733,238 A | 5/1973 | Long |
| 3,871,378 A | 3/1975 | Duncan et al. |
| 4,251,587 A | 2/1981 | Mimura et al. |
| 4,333,979 A | 6/1982 | Sciaraffa |
| 4,525,905 A | 7/1985 | Bogucki-land |
| 4,610,678 A | 9/1986 | Weisman |
| 4,640,859 A | 2/1987 | Hansen |
| 4,657,539 A | 4/1987 | Hasse |
| 4,673,402 A | 6/1987 | Weisman |
| 4,695,278 A | 9/1987 | Lawson |
| 4,704,115 A | 11/1987 | Buell |
| 4,741,941 A | 5/1988 | Englebert |
| 4,776,911 A | 10/1988 | Uda et al. |
| 4,834,735 A | 5/1989 | Alemany |
| 4,854,984 A | 8/1989 | Ball |
| 4,888,231 A | 12/1989 | Angstadt |
| 4,909,803 A | 3/1990 | Aziz |
| 4,940,464 A | 7/1990 | Van Gompel |
| 4,984,584 A * | 1/1991 | Hansen ............ B32B 5/10 428/152 |
| 5,003,676 A | 4/1991 | Mcfalls |
| 5,060,881 A | 10/1991 | Bogucki-land |
| 5,092,861 A | 3/1992 | Nomura |
| 5,110,403 A | 5/1992 | Ehlert |
| 5,167,897 A | 12/1992 | Weber |
| 5,246,433 A | 9/1993 | Hasse |
| 5,334,289 A | 8/1994 | Trokhan |
| 5,342,341 A | 8/1994 | Igaue |
| 5,360,420 A | 11/1994 | Cook |
| 5,393,360 A | 2/1995 | Bridges |
| 5,413,849 A | 5/1995 | Austin |
| 5,514,523 A | 5/1996 | Trokhan |
| 5,525,175 A | 6/1996 | Blenke et al. |
| 5,531,729 A | 7/1996 | Coles |
| 5,558,658 A | 9/1996 | Menard et al. |
| 5,562,646 A | 10/1996 | Goldman |
| 5,569,234 A | 10/1996 | Buell |
| 5,575,874 A | 11/1996 | Griesbach |

(56) References Cited

U.S. PATENT DOCUMENTS

| | | |
|---|---|---|
| 5,599,335 A | 2/1997 | Goldman |
| 5,599,420 A | 2/1997 | Yeo |
| 5,628,097 A | 5/1997 | Benson |
| 5,643,588 A | 7/1997 | Roe |
| 5,643,653 A | 7/1997 | Griesbach |
| 5,669,894 A | 9/1997 | Goldman |
| 5,674,216 A | 10/1997 | Buell |
| 5,702,551 A | 12/1997 | Huber |
| 5,775,380 A | 7/1998 | Roelstraete |
| 5,827,259 A | 10/1998 | Laux |
| 5,858,504 A | 1/1999 | Fitting |
| 5,887,322 A * | 3/1999 | Hartzheim ............ B65H 69/02 28/209 |
| 5,895,623 A | 4/1999 | Trokhan |
| 5,897,545 A | 4/1999 | Kline |
| 5,916,661 A | 6/1999 | Benson |
| 5,957,908 A | 9/1999 | Kline |
| 5,964,973 A | 10/1999 | Heath et al. |
| 5,968,025 A | 10/1999 | Roe |
| 5,993,433 A | 11/1999 | St. Louis |
| 5,997,521 A | 12/1999 | Robles et al. |
| 6,036,796 A | 3/2000 | Halbert |
| 6,043,168 A | 3/2000 | Colman |
| 6,107,537 A | 8/2000 | Elder |
| 6,107,539 A | 8/2000 | Palumbo |
| 6,118,041 A | 9/2000 | Roe |
| 6,120,487 A | 9/2000 | Ashton |
| 6,120,489 A | 9/2000 | Johnson |
| 6,139,941 A | 10/2000 | Jankevics |
| 6,153,209 A | 11/2000 | Vega |
| 6,248,195 B1 | 6/2001 | Schmitz |
| 6,248,197 B1 | 6/2001 | Nakanishi et al. |
| 6,291,039 B1 | 9/2001 | Combe |
| 6,319,239 B1 | 11/2001 | Daniels |
| 6,353,431 B1 | 3/2002 | Poole et al. |
| 6,361,638 B2 | 3/2002 | Takai |
| 6,383,431 B1 | 5/2002 | Dobrin |
| 6,395,957 B1 | 5/2002 | Chen |
| 6,410,129 B2 | 6/2002 | Zhang |
| 6,426,444 B2 | 7/2002 | Roe |
| 6,475,600 B1 | 11/2002 | Morman et al. |
| 6,478,785 B1 | 11/2002 | Ashton et al. |
| 6,482,191 B1 | 11/2002 | Roe et al. |
| 6,508,641 B1 | 1/2003 | Kubik |
| 6,545,197 B1 | 4/2003 | Muller |
| 6,554,815 B1 | 4/2003 | Umebayashi |
| 6,586,652 B1 | 7/2003 | Roe |
| 6,617,016 B2 | 9/2003 | Zhang |
| 6,627,787 B1 | 9/2003 | Roe |
| 6,632,504 B1 | 10/2003 | Gillespie |
| 6,645,330 B2 | 11/2003 | Pargass |
| 6,673,418 B1 | 1/2004 | Deolivera |
| 6,676,054 B2 | 1/2004 | Heaney |
| 6,702,798 B2 | 3/2004 | Christoffel |
| 6,790,798 B1 | 9/2004 | Suzuki |
| 6,821,301 B2 | 11/2004 | Azuse |
| 6,825,393 B2 | 11/2004 | Roe |
| 6,861,571 B1 | 3/2005 | Roe |
| 7,008,685 B2 | 3/2006 | Groitzsch |
| 7,118,558 B2 | 10/2006 | Wu |
| 7,465,367 B2 | 12/2008 | Day |
| 7,569,039 B2 | 8/2009 | Matsuda |
| 7,582,348 B2 | 9/2009 | Ando |
| 7,642,398 B2 | 1/2010 | Jaerpenberg |
| 7,708,849 B2 | 5/2010 | Mccabe |
| 7,777,094 B2 | 8/2010 | Mori |
| 7,861,756 B2 | 1/2011 | Jenquin |
| 7,878,447 B2 | 2/2011 | Hartzheim |
| 7,901,393 B2 | 3/2011 | Matsuda |
| 7,905,446 B2 | 3/2011 | Hartzheim |
| 7,954,213 B2 | 6/2011 | Mizutani |
| 8,093,161 B2 | 1/2012 | Bansal |
| 8,143,177 B2 | 3/2012 | Noda |
| 8,186,296 B2 | 5/2012 | Brown |
| 8,226,625 B2 | 7/2012 | Turner |
| 8,277,430 B2 | 10/2012 | Tabor et al. |
| 8,308,706 B2 | 11/2012 | Fukae |
| 8,377,554 B2 | 2/2013 | Martin |
| 8,388,594 B2 | 3/2013 | Turner |
| 8,440,043 B1 | 5/2013 | Schneider |
| 8,551,608 B2 | 10/2013 | Kawakami et al. |
| 8,585,666 B2 | 11/2013 | Weisman |
| 8,647,319 B2 | 2/2014 | Een |
| 8,729,332 B2 | 5/2014 | Takahashi |
| 8,778,127 B2 | 7/2014 | Schneider |
| 8,853,108 B2 | 10/2014 | Ahoniemi |
| 8,906,275 B2 | 12/2014 | Davis |
| 8,939,957 B2 | 1/2015 | Raycheck |
| 9,005,392 B2 | 4/2015 | Schneider |
| 9,039,855 B2 | 5/2015 | Schneider |
| 9,050,213 B2 | 6/2015 | Lavon |
| 9,156,648 B2 | 10/2015 | Yamamoto |
| 9,168,182 B2 | 10/2015 | Hargett |
| 9,198,804 B2 | 12/2015 | Nakamura |
| 9,226,861 B2 | 1/2016 | Lavon |
| 9,248,054 B2 | 2/2016 | Brown |
| 9,265,672 B2 | 2/2016 | Brown |
| 9,295,590 B2 | 3/2016 | Brown |
| 9,370,775 B2 | 6/2016 | Harvey |
| 9,440,043 B2 | 9/2016 | Arora |
| 9,453,303 B2 | 9/2016 | Aberg |
| 9,539,735 B2 | 1/2017 | Ferguson |
| 9,732,454 B2 | 8/2017 | Davis |
| 9,758,339 B2 | 9/2017 | Yanez, Jr. |
| 9,795,520 B2 | 10/2017 | Kaneko |
| 9,877,876 B2 | 1/2018 | Huang |
| 10,190,244 B2 | 1/2019 | Ashraf |
| 10,596,045 B2 | 3/2020 | Koshijima |
| 10,792,194 B2 | 10/2020 | Hohm |
| 10,973,699 B2 | 4/2021 | Schneider et al. |
| 11,020,282 B2 | 6/2021 | Bäck et al. |
| 11,083,637 B2 | 8/2021 | Ishikawa |
| 11,344,453 B2 * | 5/2022 | Schneider ............ A61F 13/4902 |
| 2001/0030014 A1 | 10/2001 | Kwok |
| 2002/0026660 A1 | 3/2002 | Goda |
| 2002/0046802 A1 | 4/2002 | Tachibana |
| 2002/0072723 A1 | 6/2002 | Ronn |
| 2002/0084018 A1 | 7/2002 | Ward et al. |
| 2002/0099347 A1 | 7/2002 | Chen et al. |
| 2002/0103469 A1 | 8/2002 | Chen |
| 2002/0134067 A1 | 9/2002 | Heaney |
| 2002/0153271 A1 | 10/2002 | Mcmanus |
| 2002/0177829 A1 | 11/2002 | Fell |
| 2003/0044585 A1 | 3/2003 | Taylor |
| 2003/0070780 A1 | 4/2003 | Chen |
| 2003/0087056 A1 | 5/2003 | Ducker |
| 2003/0093045 A1 | 5/2003 | Erdman |
| 2003/0119404 A1 | 6/2003 | Belau |
| 2003/0125687 A1 | 7/2003 | Gubernick et al. |
| 2003/0144643 A1 | 7/2003 | Jarpenberg |
| 2003/0203162 A1 | 10/2003 | Fenwick |
| 2003/0233082 A1 | 12/2003 | Kline |
| 2004/0006323 A1 | 1/2004 | Hall |
| 2004/0030317 A1 | 2/2004 | Torigoshi |
| 2004/0059309 A1 | 3/2004 | Nortman |
| 2004/0097895 A1 | 5/2004 | Busam |
| 2004/0127881 A1 | 7/2004 | Stevens et al. |
| 2004/0133180 A1 | 7/2004 | Mori |
| 2004/0158212 A1 | 8/2004 | Ponomarenko |
| 2004/0158217 A1 | 8/2004 | Wu |
| 2004/0219854 A1 * | 11/2004 | Groitzsch ............ A61F 13/4902 442/352 |
| 2004/0230171 A1 | 11/2004 | Ando |
| 2005/0013975 A1 | 1/2005 | Brock |
| 2005/0107764 A1 | 5/2005 | Matsuda |
| 2005/0148971 A1 | 7/2005 | Kuroda et al. |
| 2005/0230037 A1 | 10/2005 | Jenquin |
| 2005/0244640 A1 | 11/2005 | Riswick et al. |
| 2005/0267431 A1 | 12/2005 | Sasaki |
| 2006/0047260 A1 | 3/2006 | Ashton |
| 2006/0069373 A1 | 3/2006 | Schlinz |
| 2006/0087053 A1 | 4/2006 | Odonnell |
| 2006/0105075 A1 | 5/2006 | Otsubo |
| 2006/0189954 A1 | 8/2006 | Kudo |

(56) References Cited

U.S. PATENT DOCUMENTS

| | | |
|---|---|---|
| 2006/0228969 A1 | 10/2006 | Erdman |
| 2006/0270302 A1 | 11/2006 | Ando |
| 2007/0026753 A1 | 2/2007 | Neely |
| 2007/0045143 A1 | 3/2007 | Clough |
| 2007/0045144 A1 | 3/2007 | Wheeler |
| 2007/0131335 A1 | 6/2007 | Zhou |
| 2007/0141311 A1 | 6/2007 | Mleziva |
| 2007/0179466 A1 | 8/2007 | Tremblay |
| 2007/0196650 A1 | 8/2007 | Yamamoto et al. |
| 2008/0134487 A1 | 6/2008 | Hartono |
| 2008/0149292 A1 | 6/2008 | Scherb |
| 2008/0161768 A1 | 7/2008 | Baba |
| 2008/0287897 A1 | 11/2008 | Guzman |
| 2009/0177176 A1 | 7/2009 | Saito |
| 2009/0204093 A1 | 8/2009 | Vasic |
| 2009/0312730 A1 | 12/2009 | Lavon |
| 2010/0022151 A1 | 1/2010 | Malowaniec |
| 2010/0036346 A1 | 2/2010 | Hammons |
| 2010/0048072 A1 | 2/2010 | Kauschke |
| 2010/0075103 A1 | 3/2010 | Miyamoto |
| 2010/0076394 A1 | 3/2010 | Hayase |
| 2010/0248575 A1 | 9/2010 | Malz |
| 2010/0307668 A1 | 12/2010 | Lange |
| 2011/0092943 A1 | 4/2011 | Bishop |
| 2011/0118689 A1 | 5/2011 | Een |
| 2011/0120897 A1 | 5/2011 | Takahashi |
| 2011/0250378 A1 | 10/2011 | Eaton |
| 2012/0004633 A1 | 1/2012 | R. Marcelo |
| 2012/0061015 A1 | 3/2012 | Lavon |
| 2012/0061016 A1 | 3/2012 | Lavon |
| 2012/0071852 A1 | 3/2012 | Tsang et al. |
| 2012/0095429 A1 | 4/2012 | Kobayashi |
| 2012/0271267 A1 | 10/2012 | Love |
| 2012/0277713 A1 | 11/2012 | Raycheck |
| 2012/0323206 A1 | 12/2012 | Mcmorrow |
| 2013/0032656 A1 | 2/2013 | Yamamoto |
| 2013/0072887 A1 | 3/2013 | Lavon |
| 2013/0102982 A1 | 4/2013 | Nakano |
| 2013/0112584 A1 | 5/2013 | Gaspari |
| 2013/0139960 A1 | 6/2013 | Maruyama |
| 2013/0171421 A1 | 7/2013 | Weisman |
| 2013/0199696 A1 | 8/2013 | Schneider |
| 2013/0199707 A1 | 8/2013 | Schneider |
| 2013/0211356 A1 | 8/2013 | Nishikawa |
| 2013/0211363 A1 | 8/2013 | Lavon |
| 2013/0255861 A1 | 10/2013 | Schneider |
| 2013/0255862 A1 | 10/2013 | Schneider |
| 2013/0255863 A1 | 10/2013 | Lavon |
| 2013/0255864 A1 | 10/2013 | Schneider |
| 2013/0255865 A1 | 10/2013 | Brown |
| 2013/0261589 A1 | 10/2013 | Fujkawa |
| 2013/0306226 A1 | 11/2013 | Zink |
| 2014/0000794 A1 | 1/2014 | Hamilton |
| 2014/0005621 A1 | 1/2014 | Roe |
| 2014/0018759 A1 | 1/2014 | Jayasinghe |
| 2014/0041797 A1 | 2/2014 | Schneider |
| 2014/0107605 A1 | 4/2014 | Schroer, Jr. |
| 2014/0127460 A1 | 5/2014 | Xu |
| 2014/0136893 A1 | 5/2014 | Xie et al. |
| 2014/0148773 A1 | 5/2014 | Brown |
| 2014/0234575 A1 | 8/2014 | Mitsuno |
| 2014/0235127 A1 | 8/2014 | Dejesus |
| 2014/0257231 A1 | 9/2014 | Wang |
| 2014/0276517 A1 | 9/2014 | Chester |
| 2014/0288521 A1 | 9/2014 | Wade |
| 2014/0296815 A1 | 10/2014 | Takken |
| 2014/0302286 A1 | 10/2014 | Okuda |
| 2014/0305570 A1 | 10/2014 | Matsunaga |
| 2014/0324009 A1 | 10/2014 | Lee |
| 2014/0343525 A1 | 11/2014 | Roh et al. |
| 2014/0377506 A1 | 12/2014 | Eckstein |
| 2014/0377513 A1 | 12/2014 | Galie |
| 2015/0083309 A1 | 3/2015 | Long |
| 2015/0126956 A1 | 5/2015 | Raycheck |
| 2015/0136893 A1 | 5/2015 | Koskol |
| 2015/0164708 A1 | 6/2015 | Hashimoto |
| 2015/0167207 A1 | 6/2015 | Bongartz et al. |
| 2015/0173967 A1 | 6/2015 | Kreuzer |
| 2015/0230995 A1 | 8/2015 | Kaneko |
| 2015/0245958 A1 | 9/2015 | Chmielewski |
| 2015/0257941 A1 | 9/2015 | Eckstein |
| 2015/0282999 A1 | 10/2015 | Arizti |
| 2015/0320612 A1 | 11/2015 | Seitz |
| 2015/0320613 A1 | 11/2015 | Seitz |
| 2015/0320619 A1 | 11/2015 | Seitz |
| 2015/0320620 A1 | 11/2015 | Seitz |
| 2015/0320622 A1 | 11/2015 | Seitz |
| 2015/0328056 A1 | 11/2015 | Een |
| 2015/0351972 A1 | 12/2015 | Bing-wo |
| 2016/0058624 A1 | 3/2016 | Hohm |
| 2016/0058627 A1 | 3/2016 | Barnes |
| 2016/0067119 A1 | 3/2016 | Weisman |
| 2016/0100989 A1 | 4/2016 | Seitz |
| 2016/0100997 A1 | 4/2016 | Seitz |
| 2016/0106633 A1 | 4/2016 | Nagata |
| 2016/0129661 A1 | 5/2016 | Arora |
| 2016/0136009 A1 | 5/2016 | Weisman |
| 2016/0228305 A1 | 8/2016 | Gualtieri |
| 2016/0270977 A1 | 9/2016 | Surushe et al. |
| 2016/0331600 A1 | 11/2016 | Polidori |
| 2017/0014281 A1 | 1/2017 | Xie |
| 2017/0027774 A1 | 2/2017 | Ashraf |
| 2017/0029993 A1 | 2/2017 | Ashraf |
| 2017/0029994 A1 | 2/2017 | Ashraf |
| 2017/0056256 A1 | 3/2017 | Smith |
| 2017/0065461 A1 | 3/2017 | Schneider |
| 2017/0079852 A1 | 3/2017 | Fujima |
| 2017/0119595 A1 | 5/2017 | Carla |
| 2017/0191198 A1 | 7/2017 | Ashraf |
| 2017/0258650 A1 | 9/2017 | Rosati |
| 2017/0281417 A1 | 10/2017 | Ishikawa |
| 2017/0319403 A1 | 11/2017 | Bewick-sonntag |
| 2017/0348163 A1 | 12/2017 | Lakso |
| 2018/0092784 A1 | 4/2018 | Wade |
| 2018/0140473 A1 | 5/2018 | Koshijima |
| 2018/0168874 A1 | 6/2018 | Lavon |
| 2018/0168875 A1 | 6/2018 | Lavon |
| 2018/0168876 A1 | 6/2018 | Lavon |
| 2018/0168877 A1 | 6/2018 | Schneider |
| 2018/0168878 A1 | 6/2018 | Schneider |
| 2018/0168879 A1 | 6/2018 | Schneider |
| 2018/0168880 A1 | 6/2018 | Schneider |
| 2018/0168885 A1 | 6/2018 | Zink, II |
| 2018/0168887 A1 | 6/2018 | Lavon |
| 2018/0168888 A1 | 6/2018 | Zink |
| 2018/0168889 A1 | 6/2018 | Lavon |
| 2018/0168890 A1 | 6/2018 | Lavon |
| 2018/0168891 A1 | 6/2018 | Wise |
| 2018/0168892 A1 | 6/2018 | Lavon |
| 2018/0168893 A1 | 6/2018 | Ashraf |
| 2018/0169964 A1 | 6/2018 | Schneider |
| 2018/0170026 A1 | 6/2018 | Schneider |
| 2018/0170027 A1 | 6/2018 | Schneider |
| 2018/0214318 A1 | 8/2018 | Ashraf |
| 2018/0214321 A1 | 8/2018 | Ashraf |
| 2018/0216269 A1 | 8/2018 | Ashraf |
| 2018/0216270 A1 | 8/2018 | Ashraf |
| 2018/0216271 A1 | 8/2018 | Ashraf |
| 2018/0333311 A1 | 11/2018 | Maki |
| 2019/0003079 A1 | 1/2019 | Ashraf |
| 2019/0003080 A1 | 1/2019 | Ashraf |
| 2019/0070041 A1 | 3/2019 | Schneider |
| 2019/0070042 A1 | 3/2019 | Beck |
| 2019/0112737 A1 | 4/2019 | Ashraf |
| 2019/0246196 A1 | 8/2019 | Han |
| 2019/0254881 A1 | 8/2019 | Ishikawa |
| 2019/0298586 A1 | 10/2019 | Ashraf |
| 2019/0298587 A1 | 10/2019 | Ashraf |
| 2019/0374392 A1 | 12/2019 | Ninomiya |
| 2019/0374404 A1 | 12/2019 | Ninomiya |
| 2020/0155370 A1 | 5/2020 | Ohtsubo |
| 2020/0155371 A1 | 5/2020 | Ohtsubo |
| 2020/0206040 A1 | 7/2020 | Andrews |
| 2020/0214901 A1 | 7/2020 | Andrews |

(56) References Cited

U.S. PATENT DOCUMENTS

| | | | |
|---|---|---|---|
| 2020/0298545 | A1 | 9/2020 | Andrews |
| 2021/0186767 | A1 | 6/2021 | Schneider et al. |
| 2021/0275362 | A1 | 9/2021 | Schneider et al. |

FOREIGN PATENT DOCUMENTS

| | | | |
|---|---|---|---|
| CN | 1488693 A | 4/2004 | |
| CN | 1685099 A | 10/2005 | |
| CN | 1276196 C | 9/2006 | |
| CN | 101746057 | 6/2010 | |
| CN | 102712434 A | 10/2012 | |
| CN | 104244881 A | 12/2014 | |
| CN | 105997351 A | 10/2016 | |
| CN | 110022811 A | 7/2019 | |
| EP | 0989218 A1 | 3/2000 | |
| EP | 1305248 | 5/2003 | |
| EP | 1452157 | 9/2004 | |
| EP | 1473148 A1 | 11/2004 | |
| EP | 1393701 B1 | 7/2013 | |
| EP | 3056176 | 8/2016 | |
| EP | 3563817 A1 | 12/2016 | |
| EP | 3092997 B1 | 8/2017 | |
| EP | 3251642 A1 | 12/2017 | |
| EP | 3257488 A1 | 12/2017 | |
| JP | 3213543 B2 | 9/1991 | |
| JP | H03213543 A | 9/1991 | |
| JP | H0430847 A | 2/1992 | |
| JP | H06254117 A | 9/1994 | |
| JP | 8071107 A | 3/1996 | |
| JP | H08071107 | 3/1996 | |
| JP | H08132576 A | 5/1996 | |
| JP | H10179635 A | 7/1998 | |
| JP | 2000026015 A | 1/2000 | |
| JP | 2000160460 A | 6/2000 | |
| JP | 3086141 B2 | 9/2000 | |
| JP | 2001276120 A | 10/2001 | |
| JP | 2001346825 A | 12/2001 | |
| JP | 2002035029 | 2/2002 | |
| JP | 2002178428 | 6/2002 | |
| JP | 2002238934 A | 8/2002 | |
| JP | 2002248127 A | 9/2002 | |
| JP | 2003521949 A | 7/2003 | |
| JP | 2004081365 A | 3/2004 | |
| JP | 2004229857 A | 8/2004 | |
| JP | 2004237410 A | 8/2004 | |
| JP | 2004254862 A | 9/2004 | |
| JP | 2004298362 A | 10/2004 | |
| JP | 2005320636 A | 11/2005 | |
| JP | 2006149747 A | 6/2006 | |
| JP | 2006149749 A | 6/2006 | |
| JP | 2006204673 | 12/2006 | |
| JP | 2007190397 A | 8/2007 | |
| JP | 2008029749 A | 2/2008 | |
| JP | 2008055198 A | 3/2008 | |
| JP | 2008104853 A | 5/2008 | |
| JP | 2008105425 A | 5/2008 | |
| JP | 2008148942 A | 7/2008 | |
| JP | 2008154998 A | 7/2008 | |
| JP | 2008179128 A | 8/2008 | |
| JP | 2008194493 A | 8/2008 | |
| JP | 2008229006 A | 10/2008 | |
| JP | 2008229007 A | 10/2008 | |
| JP | 2008253290 | 10/2008 | |
| JP | 2008260131 A | 10/2008 | |
| JP | 2008264480 A | 11/2008 | |
| JP | 2008272250 A | 11/2008 | |
| JP | 2008272253 A | 11/2008 | |
| JP | 2008296585 A | 12/2008 | |
| JP | 2009000161 A | 1/2009 | |
| JP | 2009039341 A | 2/2009 | |
| JP | 2009056156 A | 3/2009 | |
| JP | 2009106667 A | 5/2009 | |
| JP | 2009172231 A | 8/2009 | |
| JP | 2009240804 A | 10/2009 | |
| JP | 2009241607 A | 10/2009 | |
| JP | 2010005918 A | 1/2010 | |
| JP | 2010131833 | 6/2010 | |
| JP | 2011015707 A | 1/2011 | |
| JP | 2011111165 A | 6/2011 | |
| JP | 2011178124 A | 9/2011 | |
| JP | 2011225000 A | 11/2011 | |
| JP | 2012050882 A | 3/2012 | |
| JP | 2012050883 A | 3/2012 | |
| JP | 2012115358 A | 6/2012 | |
| JP | 2012521498 A | 9/2012 | |
| JP | 5124187 B2 | 11/2012 | |
| JP | 5124188 B2 | 11/2012 | |
| JP | 2013138795 A | 7/2013 | |
| JP | 2014097257 A | 5/2014 | |
| JP | 2014111222 A | 6/2014 | |
| JP | 2014188042 A | 10/2014 | |
| JP | 2015510831 A | 4/2015 | |
| JP | 2015521499 A | 7/2015 | |
| JP | 2015171501 A | 10/2015 | |
| JP | 2016013687 A | 1/2016 | |
| JP | 2016016536 A | 2/2016 | |
| JP | 5942819 B2 | 6/2016 | |
| JP | 2016193199 | 11/2016 | |
| JP | 6149635 B2 | 6/2017 | |
| JP | 2019081304 A | 5/2019 | |
| JP | 2019115409 A | 7/2019 | |
| JP | 2019166804 A | 10/2019 | |
| JP | 2019181807 A | 10/2019 | |
| JP | 2020054741 A | 4/2020 | |
| JP | 2020054742 A | 4/2020 | |
| JP | 2020054744 A | 4/2020 | |
| JP | 2020054745 A | 4/2020 | |
| JP | 2022117131 A | 8/2022 | |
| WO | 9604874 A1 | 2/1996 | |
| WO | 9925296 A1 | 5/1999 | |
| WO | 2003015681 | 2/2003 | |
| WO | 03059603 A1 | 7/2003 | |
| WO | 2008123348 A1 | 10/2008 | |
| WO | 2011137962 A1 | 11/2011 | |
| WO | 2013084977 A1 | 6/2013 | |
| WO | 2014084168 A1 | 6/2014 | |
| WO | 2014196669 A2 | 9/2014 | |
| WO | 2016047320 A1 | 3/2016 | |
| WO | 2016056092 A1 | 4/2016 | |
| WO | 2016056093 A1 | 4/2016 | |
| WO | 2016063346 A1 | 4/2016 | |
| WO | 2016067387 A1 | 5/2016 | |
| WO | 2016071981 A1 | 5/2016 | |
| WO | 2016075974 A1 | 5/2016 | |
| WO | 2016098416 A1 | 6/2016 | |
| WO | 2016104412 A1 | 6/2016 | |
| WO | 2016104422 A1 | 6/2016 | |
| WO | 2016158499 A1 | 10/2016 | |
| WO | 2016158746 A1 | 10/2016 | |
| WO | 2016181769 A1 | 11/2016 | |
| WO | 2016208502 A1 | 12/2016 | |
| WO | 2016208513 A1 | 12/2016 | |
| WO | 2017105997 A1 | 6/2017 | |
| WO | 2018061288 A1 | 4/2018 | |
| WO | 2018084145 A1 | 5/2018 | |
| WO | 2018118882 A1 | 6/2018 | |
| WO | 2018154680 A1 | 8/2018 | |
| WO | 2018154682 A1 | 8/2018 | |
| WO | 2018167836 A1 | 9/2018 | |
| WO | 2019046363 A1 | 3/2019 | |
| WO | 2019111203 A1 | 6/2019 | |
| WO | 2019150802 A1 | 8/2019 | |
| WO | 2020006996 A1 | 1/2020 | |

OTHER PUBLICATIONS

3D Nonwovens Developments for textured nonwovens; Sep. 19, 2017, pp. 1-2.
All Office Actions, U.S. Appl. No. 15/846,382, filed Dec. 19, 2017.
All Office Actions; U.S. Appl. No. 17/189,476, filed Mar. 2, 2021.
All Office Actions; U.S. Appl. No. 17/191,772, filed Mar. 4, 2021.
All Office Actions; U.S. Appl. No. 17/198,311, filed Mar. 11, 2021.

(56) References Cited

OTHER PUBLICATIONS

American Cancer Society—What Cancer Patients Their Families and Caregivers Need to Know About COVID 19—Is Impacting Our Patient Services.
ASTM—Standard Tables of Body Measurements for Adult Females Misses Figure Type Size Range 00-20.
ASTM—Standard Tables of Body Measurements for Children Infant Size—Preemie to 24 Months.
Unpublished U.S. Appl. No. 17/189,476, filed Mar. 2, 2021, to Uwe Schneider et al.
Unpublished U.S. Appl. No. 17/191,772, filed Mar. 4, 2021, to Uwe Schneider et al.
Unpublished U.S. Appl. No. 17/198,311, filed Mar. 11, 2021, to Uwe Schneider et al.

* cited by examiner

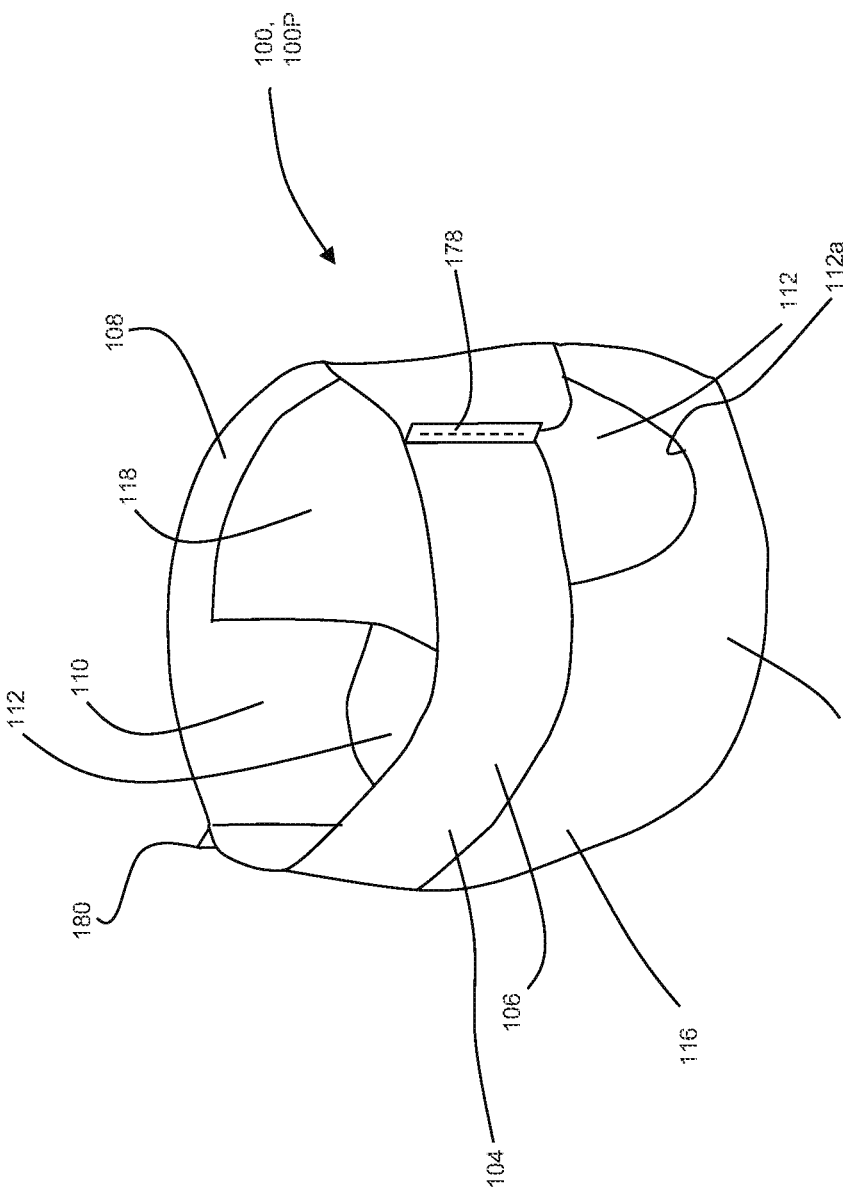

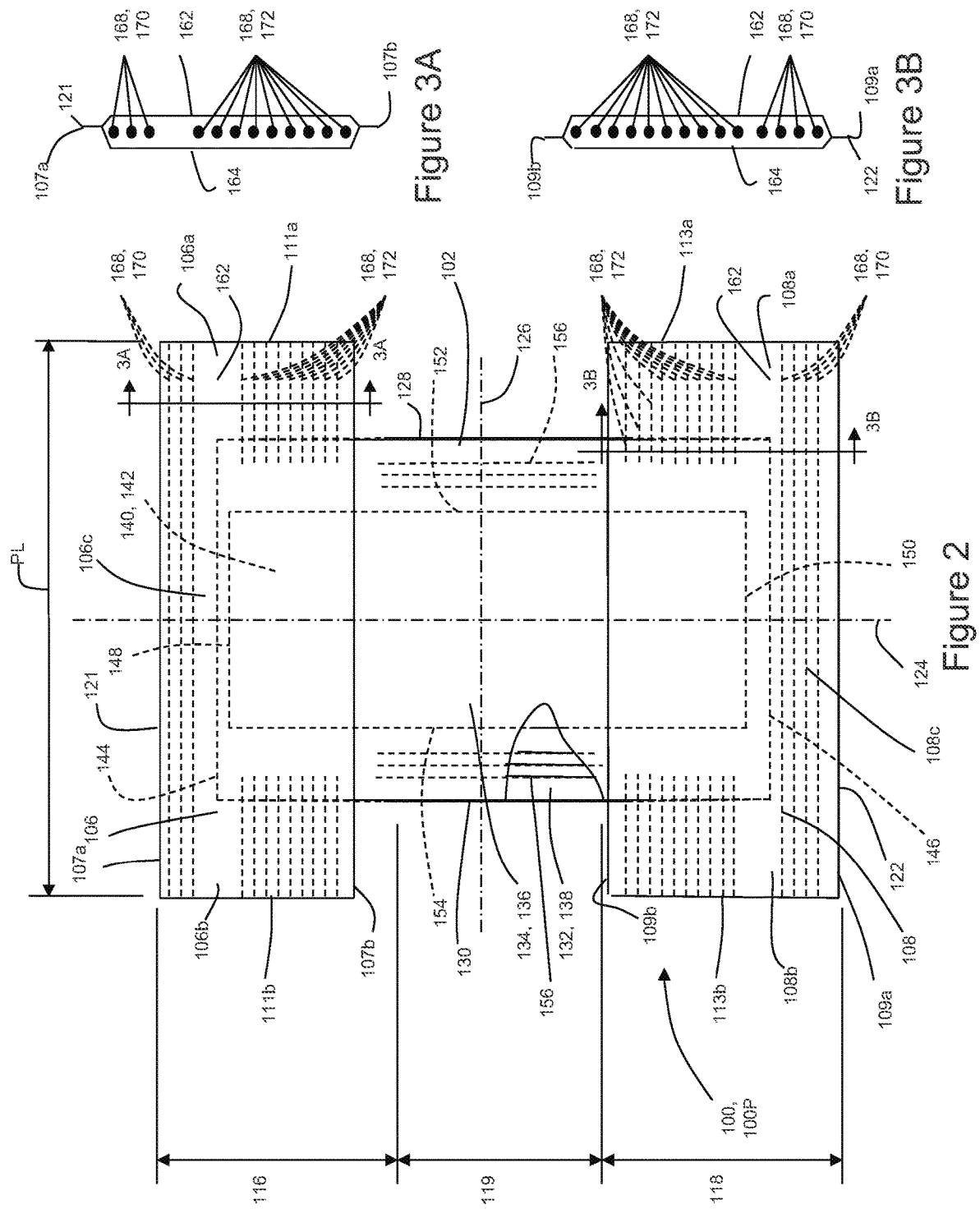

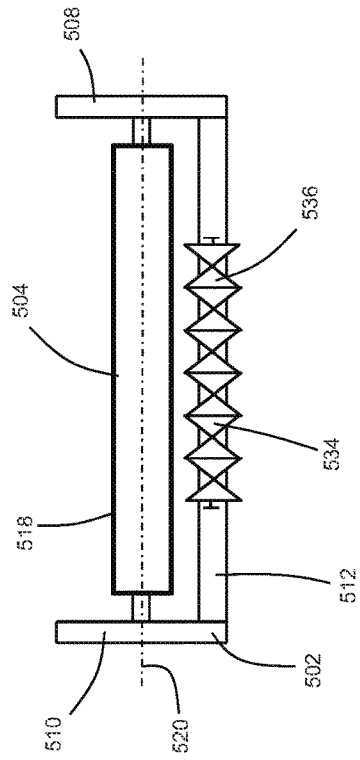
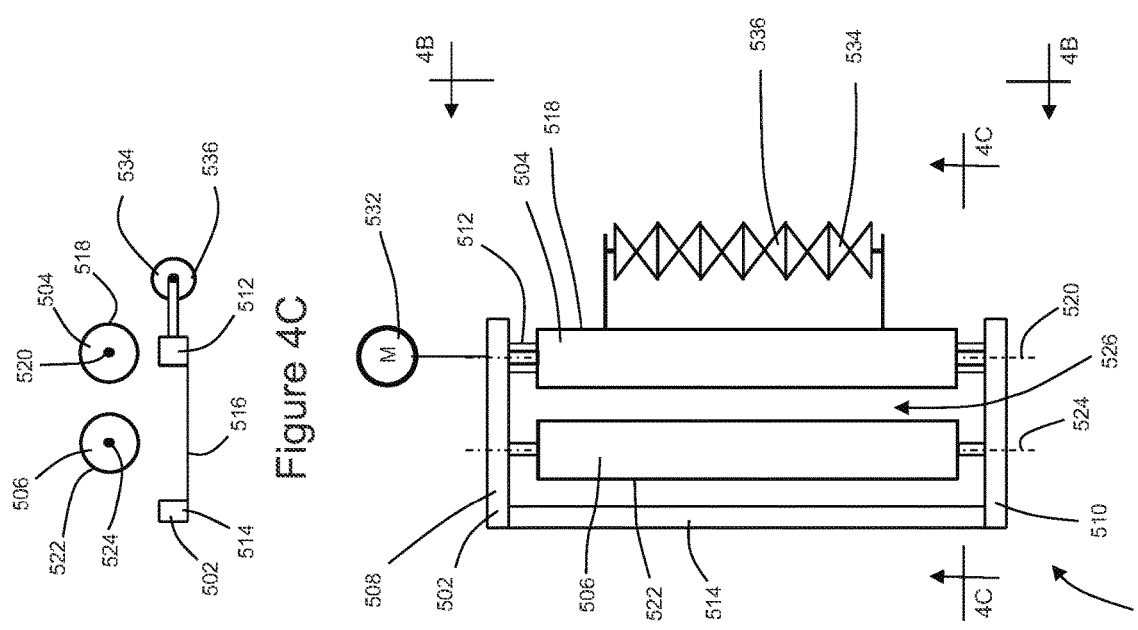

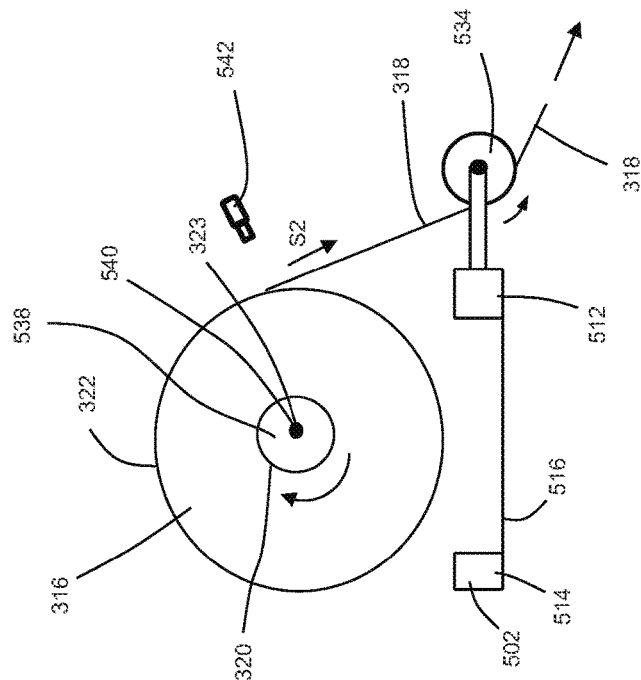
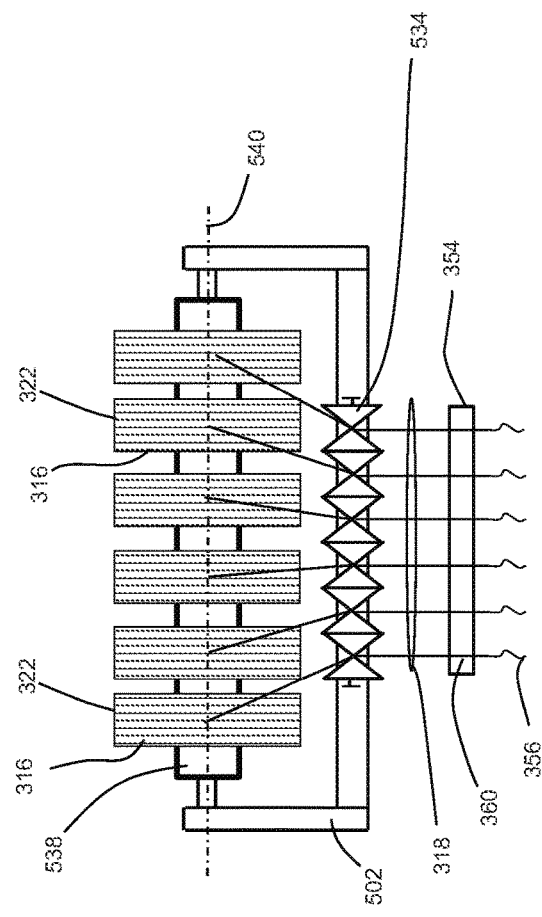
Figure 24E
Figure 24D

METHODS AND APPARATUSES FOR MAKING ELASTOMERIC LAMINATES WITH ELASTIC STRANDS UNWOUND FROM SPOOLS ON SURFACE UNWINDERS

CROSS-REFERENCE TO RELATED APPLICATIONS

This application is a continuation of, and claims priority under 35 U.S.C. § 120 to, U.S. patent application Ser. No. 17/191,772, filed on Mar. 4, 2021, which is a continuation of, and claims priority under 35 U.S.C. § 120 to, U.S. patent application Ser. No. 15/846,382, filed on Dec. 19, 2017, which claims the benefit, under 35 USC 119(e), to U.S. Provisional Patent Application No. 62/436,589, filed on Dec. 20, 2016; U.S. Provisional Patent Application No. 62/483,965, filed on Apr. 11, 2017; U.S. Provisional Patent Application No. 62/553,149, filed on Sep. 1, 2017; U.S. Provisional Patent Application No. 62/553,171, filed on Sep. 1, 2017; U.S. Provisional Patent Application No. 62/553,538, filed on Sep. 1, 2017; and U.S. Provisional Patent Application No. 62/581,278, filed on Nov. 3, 2017; each of which are herein incorporated by reference in their entirety.

FIELD OF THE INVENTION

The present disclosure relates to methods for manufacturing absorbent articles, and more particularly, to apparatuses and methods for making elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers between the locations where the nonwoven is bonded to the elastic strands, and in turn, forms corrugations. The resulting elastomeric laminate is stretchable to the extent that the corrugations allow the elastic strands to elongate.

In some assembly processes, stretched elastic strands may be advanced in a machine direction and adhered between two advancing substrates, wherein the stretched elastic strands are spaced apart from each other in a cross direction. Some assembly processes are also configured to drawing elastic strands from rotating spools arranged along a cross direction on a surface unwinding device. However, problems can be encountered in manufacturing processes when drawing elastic strands from spools. For example, when elastic strands are completely drawn from a spool, a new spool of elastics will be needed to replace the empty spool. As such, in some configurations, an entire manufacturing line may need to be temporarily stopped while the empty spool is replaced. Some manufacturing lines may operate at relatively slow speeds, and as such, these manufacturing lines can be temporarily stopped to replace empty spools and may not result in a major disruption to production. However, some manufacturing lines, such as disposable absorbent article manufacturing lines, may operate at high speeds and/or would require depleted spools of elastics to be replaced relatively often. As such, it can be inefficient and/or cost prohibitive to frequently stop and restart high speed manufacturing operations to replace empty spools.

Consequently, it would be beneficial to provide a method and apparatus for producing elastomeric laminates with spools of elastic strands that can be replaced without having to stop the assembly process.

SUMMARY OF THE INVENTION

In one form, a method for making an elastomeric laminate comprises the steps of: providing first spools, each first spool comprising an outer circumferential surface defined by an elastic strand wound onto a core; positioning the outer circumferential surface of each first spool in rolling contact with a first roll; providing second spools, each second spool comprising an outer circumferential surface defined by an elastic strand wound onto a core; positioning the outer circumferential surface of each second spool in rolling contact with a second roll; unwinding elastic strands from the first spools by advancing the elastic strands from between each first spool and the first roll; combining the elastic strands from the first spools with a first substrate and a second substrate; unwinding elastic strands from the second spools by advancing the elastic strands from between each second spool and the second roll; connecting the elastic strands from the second spools with a splicer member; combining the splicer member and the elastic strands from the second spools with the elastic strands from the first spools between the first and second substrates; and subsequently discontinuing unwinding of the elastic strands from the first spools.

In another form, a method for making an elastomeric laminate comprises the steps of: providing first spools, each first spool comprising an outer circumferential surface defined by an elastic strand wound onto a core; positioning the outer circumferential surface of each first spool in rolling contact with a first roll; providing second spools, each second spool comprising an outer circumferential surface defined by an elastic strand wound onto a core; positioning the outer circumferential surface of each second spool in rolling contact with a second roll; rotating a roller about a first axis of rotation extending in a cross direction, the roller comprising an outer circumferential surface; providing a first substrate and a second substrate, each comprising a first surface and an opposing second surface; advancing the first surface of the first substrate onto the outer circumferential surface of the roller; rotating the first spools and the first roll in opposite directions; unwinding elastic strands from the first spools by advancing the elastic strands from between each rotating first spool and the rotating first roll; advancing the first surface of the second substrate onto the second surface of the first substrate such that the elastic strands from the first spools and the first substrate are positioned between the second substrate and the outer circumferential surface of the roller; advancing the combined first substrate, second substrate, and the elastic strands from the first spools in the machine direction from the roller; rotating the second spools and the second roll in opposite directions; unwinding elastic strands from the second spools by advancing the elastic strands from between each rotating second spool and the rotating second roll; advancing the elastic strands from the second spools in between the second surface of the first substrate and the first surface of the second substrate such that the elastic strands from the first and second spools and the first substrate are positioned between the second substrate and the outer circumferential surface of the roller; and subsequently discontinuing advancement of the elastic strands from the first spools onto the second surface of the first substrate.

In yet another form, a method for making an elastomeric laminate comprises the steps of: advancing a first substrate and a second substrate in a machine direction, the first and second substrates each comprising a first surface and an opposing second surface; providing first spools, each first spool comprising an outer circumferential surface defined by an elastic strand wound onto a cylindrical core, each cylindrical core extending axially through each first spool; providing a first roll comprising an outer circumferential surface; positioning the outer circumferential surface of each first spool in rolling contact with the outer circumferential surface of the first roll; rotating the first spools and the first roll in opposite directions; unwinding elastic strands from the first spools by advancing the elastic strands from between each rotating first spool and the rotating first roll; positioning the elastic strands from the first spools between the second surface of the first substrate and the first surface of the second substrate; providing second spools, each spool comprising an outer circumferential surface defined by an elastic strand wound onto a cylindrical core, each cylindrical core extending axially through each second spool; providing a second roll comprising an outer circumferential surface; positioning the outer circumferential surface of each second spool in rolling contact with the outer circumferential surface of the second roll; connecting the elastic strands from the second spools with a splicer member; rotating the second spools and the second roll in opposite directions; unwinding elastic strands from the second spools by advancing the elastic strands from between each rotating second spool and the rotating second roll; combining the splicer member and the elastic strands from the second spools with the elastic strands from the first spools between the second surface of the first substrate and the first surface of the second substrate; and subsequently discontinuing advancement of the elastic strands from the first spools.

In yet another form, a method for making an elastomeric laminate comprises the steps of: providing first spools, each first spool comprising an outer circumferential surface defined by an elastic strand wound onto a core; positioning the cores of each first spool on a first mandrel; providing second spools, each second spool comprising an outer circumferential surface defined by an elastic strand wound onto a core; positioning the cores of each second spool on a second mandrel; unwinding elastic strands from the first spools by advancing the elastic strands from the outer circumferential surface of each first spool; combining the elastic strands from the first spools with a first substrate and a second substrate; unwinding elastic strands from the second spools by advancing the elastic strands from the outer circumferential surface of each second spool; connecting the elastic strands from the second spools with a splicer member; combining the splicer member and the elastic strands from the second spools with the elastic strands from the first spools between the first and second substrates; and subsequently discontinuing unwinding of the elastic strands from the first spools.

BRIEF DESCRIPTION OF THE DRAWINGS

FIG. 1A is a front perspective view of a diaper pant.

FIG. 2 is a partially cut away plan view of the diaper pant shown in FIGS. 1A and 1B in a flat, uncontracted state.

FIG. 3A is a cross-sectional view of the diaper pant of FIG. 2 taken along line 3A-3A.

FIG. 3B is a cross-sectional view of the diaper pant of FIG. 2 taken along line 3B-3B.

FIG. 4A is a top side view of an unwinder.

FIG. 4B is a front side view of the unwinder from FIG. 4A taken along line 4B-4B.

FIG. 4C is a left side view of the unwinder from FIG. 4A taken along line 4C-4C.

FIG. 24D is a front side view of spools positioned on the unwinder from FIG. 24B.

FIG. 24E is a left side view of one or more spools positioned on the unwinder from FIG. 24C.

DETAILED DESCRIPTION OF THE INVENTION

Figure 1B:
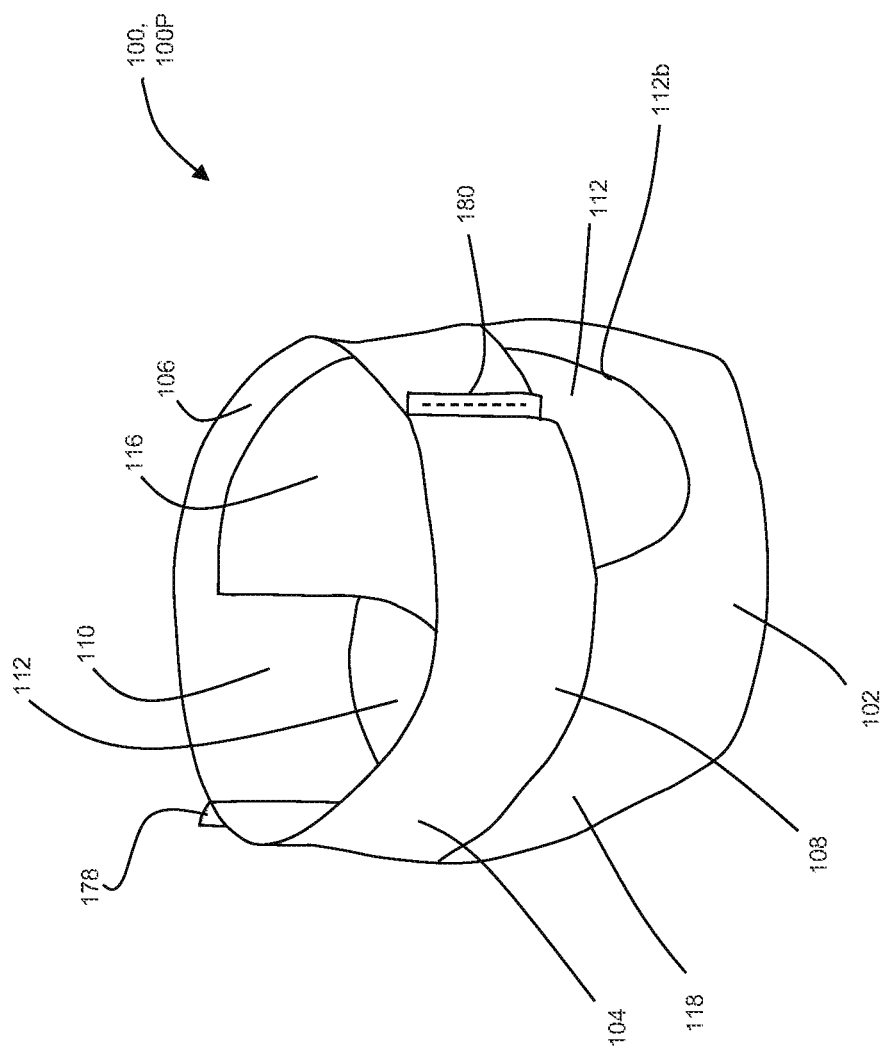
FIG. 1B is a rear perspective view of a diaper pant.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. $1/10$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861

A1; 2013/0255862 A1; 2013/0255863 A1; 2013/0255864 A1; and 2013/0255865 A1, all of which are incorporated by reference herein.

The present disclosure relates to methods for manufacturing absorbent articles, and in particular, to methods for making elastomeric laminates that may be used as components of absorbent articles. The elastomeric laminates may include a first substrate, a second substrate, and an elastic material located between the first substrate and second substrate. During the process of making the elastomeric laminate, the elastic material may be advanced and stretched in a machine direction and may be joined with either or both the first and second substrates advancing in the machine direction.

The methods and apparatuses according to the present disclosure may be configured with a first unwinder and a second unwinder. One or more first spools are positioned on the first unwinder, and one or more second spools are positioned on the second unwinder. The first and second unwinders each includes a roll rotatably connected with a frame. The first spools each comprise an outer circumferential surface defined by a first elastic strand wound onto a core, and the second spools each comprise an outer circumferential surface defined by a second elastic strand wound onto a core. The first spools are arranged on the first unwinder such that outer circumferential surface of each first spool is in rolling contact with the roll, and second spools are arranged on the second unwinder such that outer circumferential surface of each second spool is in rolling contact with the roll. During assembly of an elastomeric laminate, the first spools and the roll of the first unwinder are rotated in opposite directions, and the first elastic strands are unwound from the first spools by advancing the first elastic strands from between each first spool and the roll. The first elastic strands advance in a machine direction and are positioned between a first substrate and a second substrate to form the elastomeric laminate. The first elastic strands may also be stretched in the machine direction while advancing from the first spools to the first and second substrates. Before the first elastic strands are completely unwound from the first spools, the second spools and the roll of the second unwinder are rotated in opposite directions, and the second elastic strands are unwound from the second spools by advancing the second elastic strands from between each second spool and the roll. The second elastic strands are advanced in the machine direction from the second unwinder to between the first substrate and the second substrate such that the first and second elastic strands are positioned between the first and second substrates. Subsequently, the advancement of the first elastic strands from the first unwinder is discontinued. As such, the elastomeric laminate assembly process may continue uninterrupted while switching from an initially utilized elastic material drawn from the rotating first spools to a subsequently utilized elastic material drawn from the rotating second spools.

As previously mentioned, the elastomeric laminates made according to the processes and apparatuses discussed herein may be used to construct various types of components used in the manufacture of different types of absorbent articles, such as diaper pants and taped diapers. To help provide additional context to the subsequent discussion of the process embodiments, the following provides a general description of absorbent articles in the form of diapers that include components including the elastomeric laminates that may be produced with the methods and apparatuses disclosed herein.

FIGS. 1A, 1B, and 2 show an example of an absorbent article 100 in the form of a diaper pant 100P that may include components constructed from elastomeric laminates assembled in accordance with the apparatuses and methods disclosed herein. In particular, FIGS. 1A and 1B show perspective views of a diaper pant 100P in a pre-fastened configuration, and FIG. 2 shows a plan view of the diaper pant 100P with the portion of the diaper that faces away from a wearer oriented toward the viewer. The diaper pant 100P includes a chassis 102 and a ring-like elastic belt 104. As discussed below in more detail, a first elastic belt 106 and a second elastic belt 108 are bonded together to form the ring-like elastic belt 104.

With continued reference to FIG. 2, the diaper pant 100P and the chassis 102 each include a first waist region 116, a second waist region 118, and a crotch region 119 disposed intermediate the first and second waist regions. The first waist region 116 may be configured as a front waist region, and the second waist region 118 may be configured as back waist region. The diaper 100P may also include a laterally extending front waist edge 121 in the front waist region 116 and a longitudinally opposing and laterally extending back waist edge 122 in the back waist region 118. To provide a frame of reference for the present discussion, the diaper 100P and chassis 102 of FIG. 2 are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, and 2, the diaper pant 100P may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100P may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100P is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100P may include a backsheet 136. The backsheet 136 may also define the outer surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100P may include a topsheet 138. The topsheet 138 may also define all or part of the inner surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539.

As mentioned above, the diaper pant 100P may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834, 735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/ 0097895 A1.

As previously mentioned, the diaper 100P may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695, 278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIG. 2, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 118 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100P. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

As previously mentioned, apparatuses and methods according to the present disclosure may be utilized to produce elastomeric laminates that may be used to construct various components of diapers, such as elastic belts, leg cuffs, and the like. For example, FIGS. 4A-23 show schematic views of converting apparatuses 300 adapted to manufacture elastomeric laminates 302. As described in more detail below, the converting apparatuses 300 shown in FIGS. 4A-23 operate to advance a continuous length of elastic material 304, a continuous length of a first substrate 306, and a continuous length of a second substrate 308 along a machine direction MD. It is also to be appreciated that in some configurations, the first substrate and second substrate 306, 308 herein may be defined by two discrete substrates or may be defined by folded portions of a single substrate. The apparatus 300 stretches the elastic material 304 and joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films.

It is to be appreciated that the elastomeric laminates 302 can be used to construct various types of absorbent article components. It also to be appreciated that the methods and apparatuses herein may be adapted to operate with various types of absorbent article assembly processes, such as disclosed for example in U.S. Patent Publication Nos. 2013/0255861 A1; 2013/0255862 A1; 2013/0255863 A1; 2013/0255864 A1; and 2013/0255865 A1. For example, the elastomeric laminates 302 may be used as a continuous length of elastomeric belt material that may be converted into the first and second elastic belts 106, 108 discussed above with reference to FIGS. 1-3B. As such, the elastic material 304 may correspond with the belt elastic material 168 interposed between the outer layer 162 and the inner layer 164, which in turn, may correspond with either the first and/or second substrates 306, 308. In other examples, the elastomeric laminates may be used to construct waistbands and/or side panels in taped diaper configurations. In yet other examples, the elastomeric laminates may be used to construct various types of leg cuff and/or topsheet configurations.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, a metering device may comprise an unwinder with spools of elastic strands positioned thereon. During operation, elastic material may advance in a machine direction from rotating first spools on a first unwinder to a downstream metering device to be joined with one or more advancing substrates. Before the elastic material is completely drawn from or removed from the first spools, elastic material may also be advanced in the machine direction from rotating second spools on a second unwinder to the downstream metering device to be joined with one or more advancing substrates. Subsequently, advancement of the elastic material from the first spools to the downstream metering device may be discontinued. As such, the elastomeric laminate assembly process continues uninterrupted while replacing elastic material unwound from the first spools with elastic material unwound from the second spools. Thus, the empty first unwinder may be replaced with another unwinder with spools of elastic material positioned thereon without interrupting and/or stopping the assembly of the elastomeric laminate.

FIGS. 4A-4C show an example of an unwinder 500 that may include a frame 502, a first roll 504, and a second roll 506, wherein the first roll 504 and the second roll 506 are rotatably connected with the frame 502. It is to be appreciated that the frame 502 may be configured in various ways.

For example, the frame 502 may include a first side 508 and a second side 510. The frame 502 may also include a first cross member 512 and a second cross member 514, wherein the first and second sides 508, 510 may be connected with and separated by the first and second cross members 512, 514. The frame 502 may also include a bottom side 516.

With continued reference to FIGS. 4A-4C, the first roll 504 may be rotatably connected with the first side 508 and the second side 510 of the frame 502, and the first roll 504 includes an outer circumferential surface 518 and may be adapted to rotate about a first rotation axis 520. The second roll 506 may also be rotatably connected with the first side 508 and the second side 510 of the frame 502, and the second roll 506 includes an outer circumferential surface 522 and may be adapted to rotate about a second rotation axis 524. The first and second rolls 504, 506 may have the same or different diameters and may be connected with the frame 502 so as to define a gap 526 between the outer circumferential surface 518 of the first roll 504 and the outer circumferential surface 522 of the second roll 506. The first rotation axis 520 and the second rotation axis 524 may also be parallel or substantially parallel with each other and may be positioned at the same or different elevations. As discussed in more detail below, one or more spools 316 may be positioned on the unwinder 500. As shown in FIG. 4D, the spool 316 may include an elastic strand 318 wound onto a core 320. The spool 316 may be cylindrically shaped and include an outer circumferential surface 322 defined by the elastic strand 318 wound around the core 320. The spool 316 may also be adapted to rotate about an axis of rotation 323. The core 320 may be cylindrically shaped and the axis of rotation 323 may extend axially through the center of the core 320. Also, as an elastic strand 318 is drawn from a rotating spool 316 supported on the first roll 504 and second roll 506, the outer diameter of the spool 316 becomes smaller, and as such, the elevation of the axis of rotation 323 of the spool 316 changes. It is also to be appreciated that the spools 316 positioned on an unwinder 500 may have the same or different outer diameters and may have the axis of rotation 323 at the same or different elevations relative to each other.

Figure 4E:
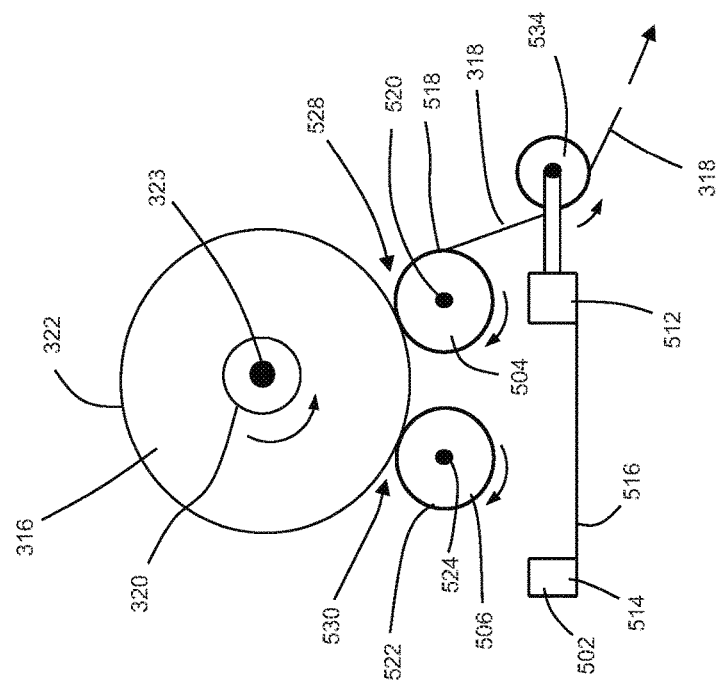
FIG. 4E is a left side view of one or more spools positioned on the unwinder from FIG. 4C.
Figure 4D:
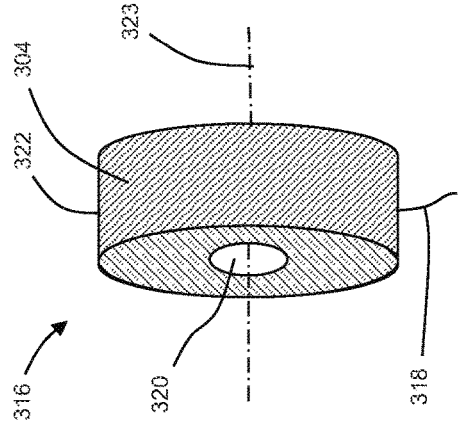
FIG. 4D is an isometric view of a spool of an elastic strand wound onto a core.

As shown in FIG. 4E, one or more spools 316 may be positioned on the unwinder 500 and supported by the first roll 504 and the second roll 506. More particularly, the outer circumferential surfaces 322 of each spool 316 may be in rolling contact with the outer circumferential surface 518 of the first roll 504 and the outer circumferential surface 522 of the second roll 506. As such, a first nip 528 is defined between the outer circumferential surface 322 of the spool 316 and the outer circumferential surface 518 of the first roll 504, and a second nip 530 is defined between the outer circumferential surface 322 of the spool 316 and the outer circumferential surface 522 of the second roll 506. During operation, each spool 316 and the first roll 504 are rotated in opposite directions, and each spool 316 and the second roll 506 are rotated in opposite directions. The elastic strand 318 advances from the rotating spool 316 through the first nip 528 to downstream assembly operations, such as described below. It is to be appreciated that the first roll 504 or the second roll 506 may be configured to drive and cause rotation of the spools 316. For example, FIG. 4A shows the first roll 504 connected with a rotation driver 532, such as a motor or a servo motor, to drive and control the rotation of the first roll 504. In some configurations, the second roll 506 may be connected with the rotation driver 532 to drive and control the rotation of the second roll 506. In turn, the rotation of the driven first roll 504 or second roll 506 causes the spools 316 to rotate. In addition, the first roll 504 or the second roll 506 may be configured as an idler that rotates as a result of the rotation of the spools 316.

Figure 7:
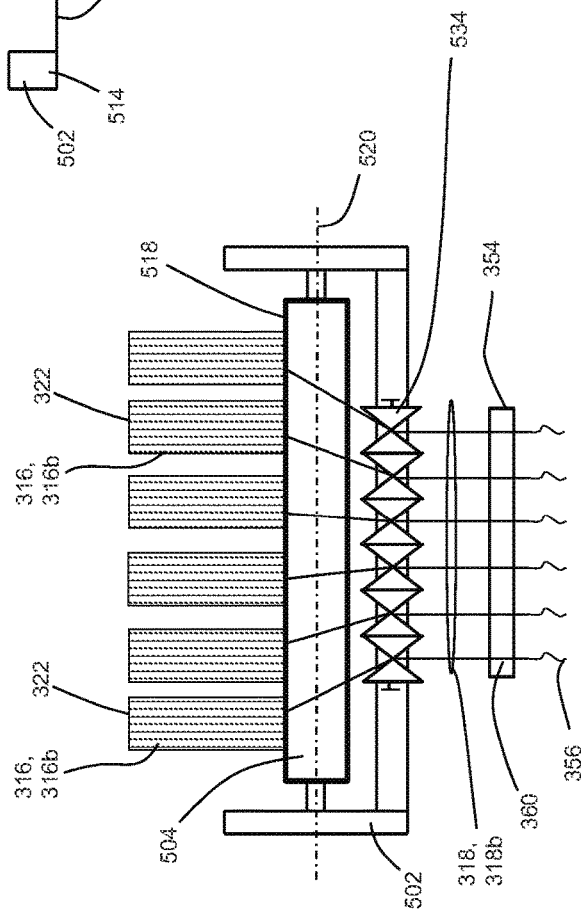
FIG. 7 is a view of the converting apparatus of FIG. 5 taken along line 7-7.
Figure 5:
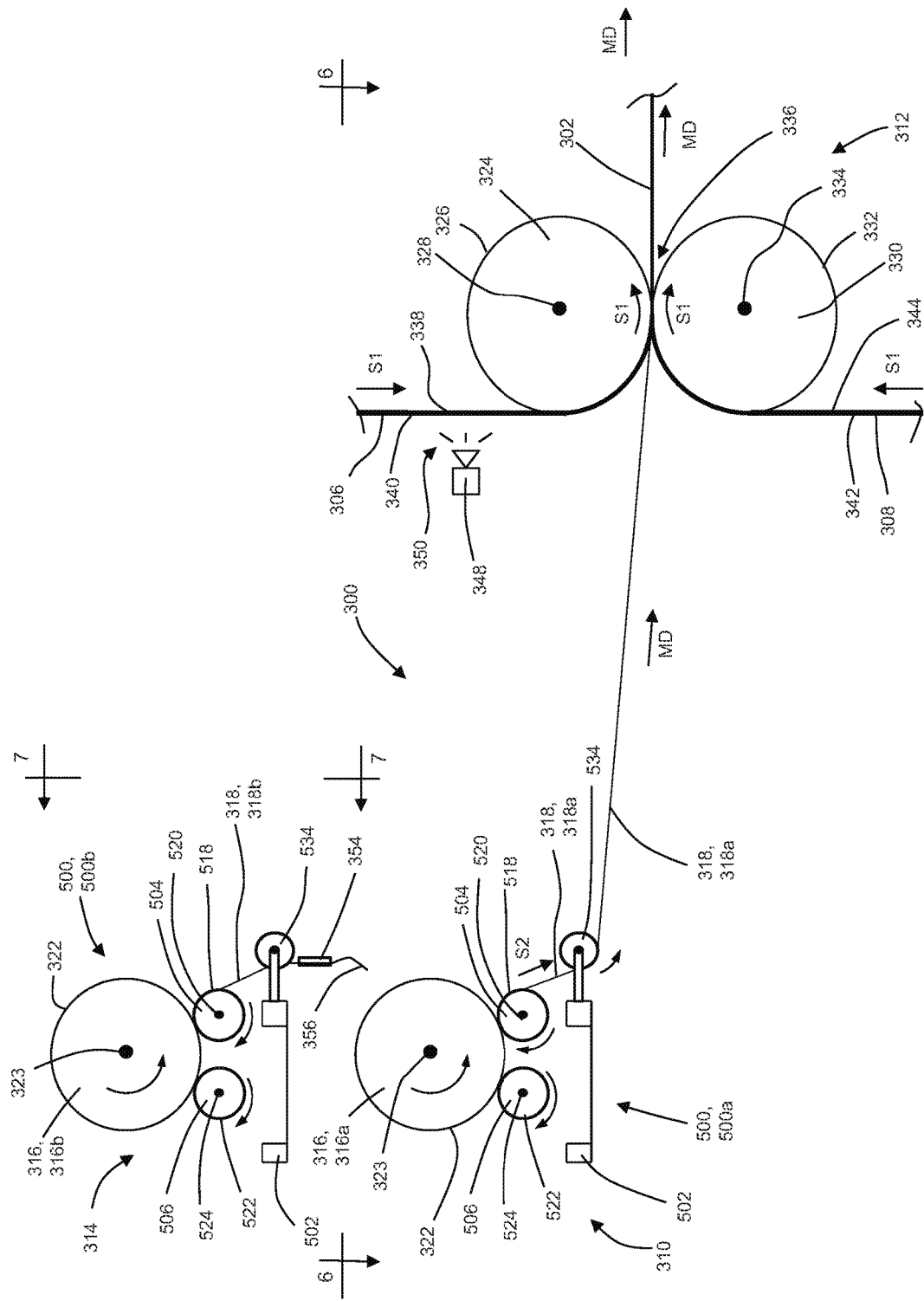
FIG. 5 is a schematic side view of a converting apparatus adapted to manufacture an elastomeric laminate including a first plurality of elastic strands positioned between a first substrate and a second substrate.
Figure 6:
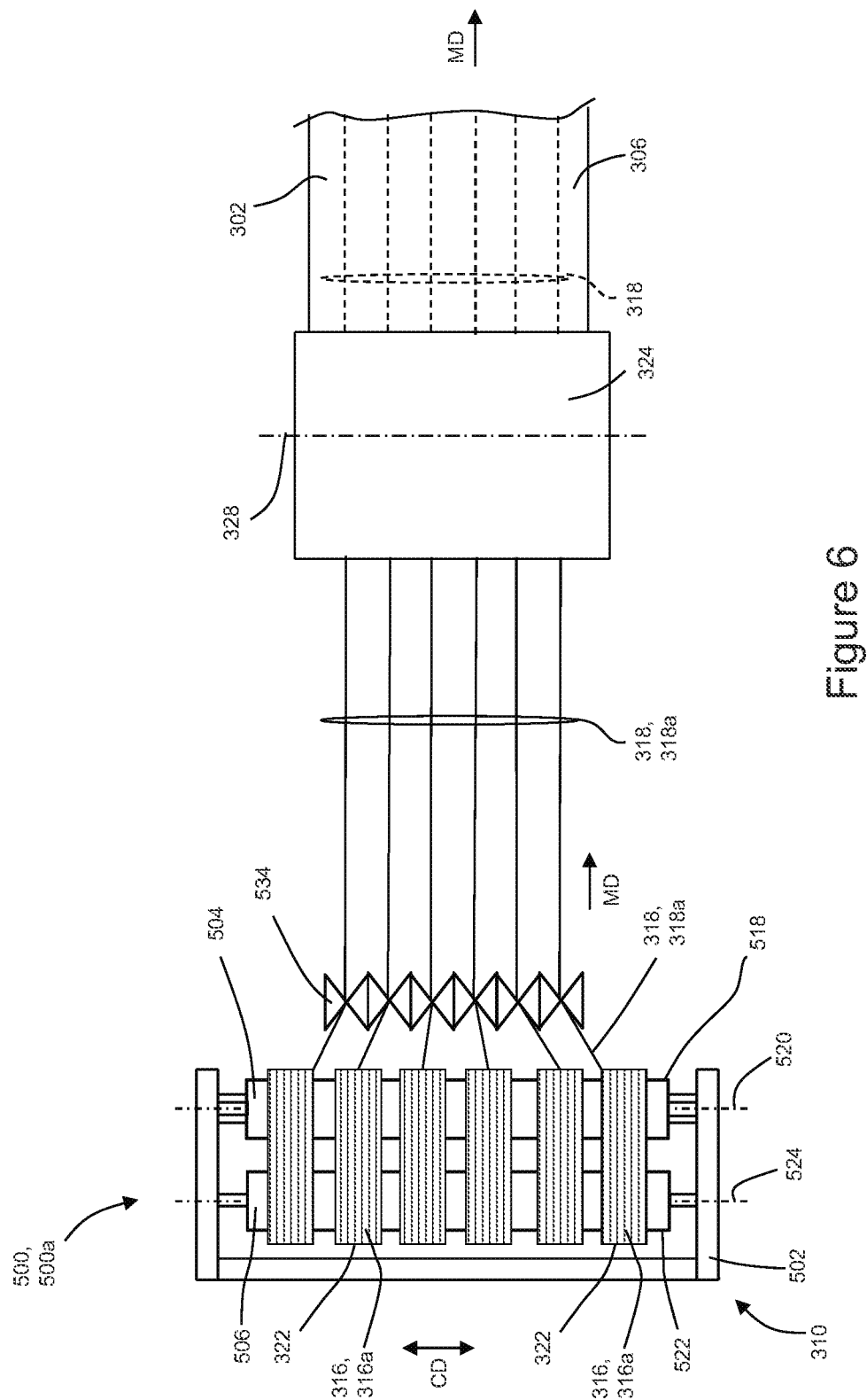
FIG. 6 is a view of the converting apparatus of FIG. 5 taken along line 6-6.

As shown in FIGS. 5-7, a converting apparatus 300 for producing an elastomeric laminate 302 may include a first metering device 310, a second metering device 312, and a third metering device 314. The first metering device 310 may be configured as a first unwinder 500a with one or more first spools 316a of first elastic strands 318a positioned thereon, and the third metering device 314 may be configured as a second unwinder 500b with one or more second spools 316b of second elastic strands 318b positioned thereon. During operation, the first elastic strands 318a advance in the machine direction MD from the first unwinder 500a to the second metering device 312. In addition, the first elastic strands 318a may be stretched along the machine direction MD between the first unwinder 500a and the second metering device 312. The stretched first elastic strands 318a are also joined with a first substrate 306 and a second substrate 308 at the second metering device 312 to produce an elastomeric laminate 302. As discussed in more detail below, once the first spools 316a are empty or nearly depleted of first elastic strands 318a, the second elastic strands 318b can be introduced into the assembly operation as replacements for the first elastic stands 318a without having to stop the assembly operation.

As shown in FIG. 5, the second metering device 312 includes: a first roller 324 having an outer circumferential surface 326 and rotates about a first axis of rotation 328, and a second roller 330 having an outer circumferential surface 332 and rotates about a second axis of rotation 334. The first roller 324 and the second roller 330 rotate in opposite directions, and the first roller 324 is adjacent the second roller 330 to define a nip 336 between the first roller 324 and the second roller 330. The first roller 324 rotates such that the outer circumferential surface 326 has a surface speed S1, and the second roller 330 may rotate such that the outer circumferential surface 332 has the same, or substantially the same, surface speed S1.

As shown in FIGS. 5 and 6, the first substrate 306 includes a first surface 338 and an opposing second surface 340, and the first substrate 306 advances to the first roller 324. In particular, the first substrate 306 advances at speed S1 to the first roller 324 where the first substrate 306 partially wraps around the outer circumferential surface 326 of the first roller 324 and advances through the nip 336. As such, the first surface 338 of the first substrate 306 travels in the same direction as and in contact with the outer circumferential surface 326 of the first roller 324. In addition, the second substrate 308 includes a first surface 342 and an opposing second surface 344, and the second substrate 308 advances to the second roller 330. In particular, the second substrate 308 advances at speed S1 to the second roller 330 where the second substrate 308 partially wraps around the outer circumferential surface 332 of the second roller 330 and advances through the nip 336. As such, the second surface 344 of the second substrate 308 travels in the same direction as and in contact with the outer circumferential surface 332 of the second roller 330.

With continued reference to FIGS. 5 and 6, the first unwinder 500a includes the first spools 316a of first elastic strands 318a wound thereon, and each first spool 316a is rotatable about a respective axis of rotation 323. As discussed above, the first spools 316a and the first roll 504 of the first unwinder 500a rotate in opposite directions, and the first spools 316a and the first roll 504 may rotate such that the outer circumferential surface 322 of the first spools 316a and the outer circumferential surface 518 of the first roll 504 move at a speed S2. As the first spools 316a rotate, the first elastic strands 318a unwind from the rotating first spools 316a and advance from the first nip 528 between each first spool 316a and the first roll 504 at the speed S2 with the first elastic strands 318a being spaced apart from each other in the cross direction CD. From the first unwinder 500a, the first elastic strands 318 advance in the machine direction MD to the nip 336. In some configurations, the speed S2 is less than the speed S1, and as such, the first elastic strands 318a are stretched in the machine direction MD. In turn, the stretched first elastic strands 318a advance through the nip 336 between the first and second substrates 306, 308 such that the first elastic strands 318a are joined with the second surface 340 of the first substrate 306 and the first surface 342 of the second substrate 308 to produce a continuous length of elastomeric laminate 302. As shown in FIG. 5, the first substrate 306 may advance past an adhesive applicator device 348 that applies adhesive 350 to the second surface 340 of the first substrate 306 before advancing to the nip 336. It is to be appreciated that the adhesive 350 may be applied to the first substrate 306 upstream of the first roller 324 and/or while the first substrate 306 is partially wrapped around the outer circumferential surface 326 of the first roller 324. It is to be appreciated that adhesive may be applied to the elastic strands 318 before and/or while being joined with first substrate 306 and second substrate 308. In addition, it is to be appreciated that adhesive may be applied to the first surface 342 of the second substrate 308 before or while being joined with the elastic strands 318 and the first substrate 306. It is also to be appreciated that the elastic strands 318 may be bonded with the first substrate 306 and/or second substrate 308 with various methods and apparatuses, such as described in U.S. Patent Application Nos. 62/436,589; 62/483,965; 62/553,538; 62/553,149; 62/553,171, and 62/581,278 and combinations thereof.

As previously discussed, the second unwinder 500b includes second elastic strands 318b positioned thereon and configured to replace the first elastic stands 318a once the first spools 316a on the first unwinder 500a are completely depleted or nearly depleted of first elastic strands 318a. As shown in FIGS. 5 and 7, the second unwinder 500b includes the second spools 316b of second elastic strands 318b wound thereon, and each second spool 316b is rotatable about a respective axis of rotation 323. As discussed above, the second spools 316b and the first roll 504 of the second unwinder 500b rotate in opposite directions, and the second spools 316b and the first roll 504 may rotate such that the outer circumferential surface 322 of the second spools 316b and the outer circumferential surface 518 of the first roll 504 move at a speed S2. As the second spools 316b rotate, the second elastic strands 318b unwind from the rotating second spools 316b and advance from the first nip 528 between each second spool 316b and the first roll 504 at the speed S2 with the second elastic strands 318b being spaced apart from each other in the cross direction CD.

Figure 8:
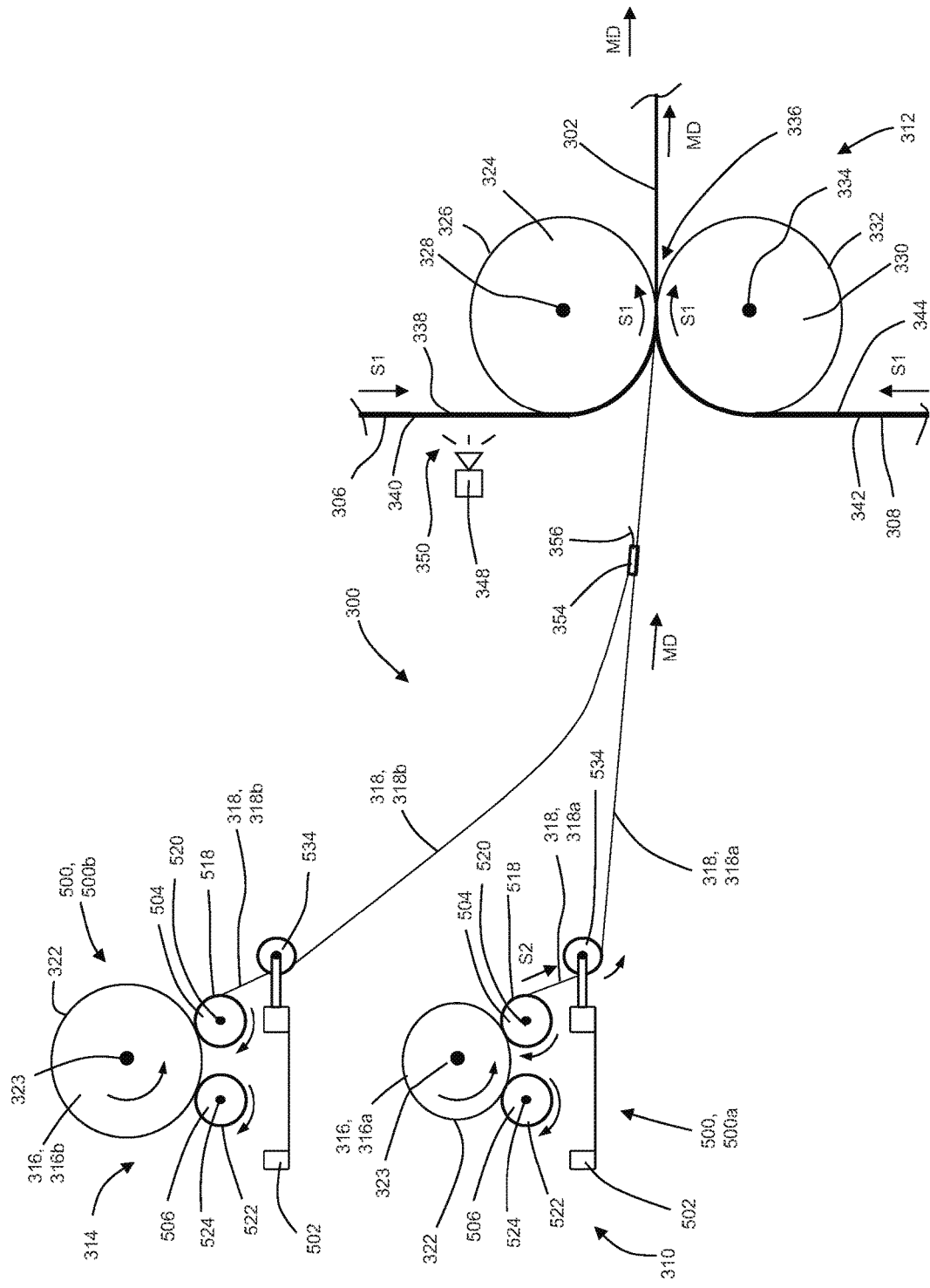
FIG. 8 is a schematic side view of the converting apparatus of FIG. 5 showing a second plurality of elastic strands connected with a first plurality of elastic strands upstream of a nip.
Figure 9:
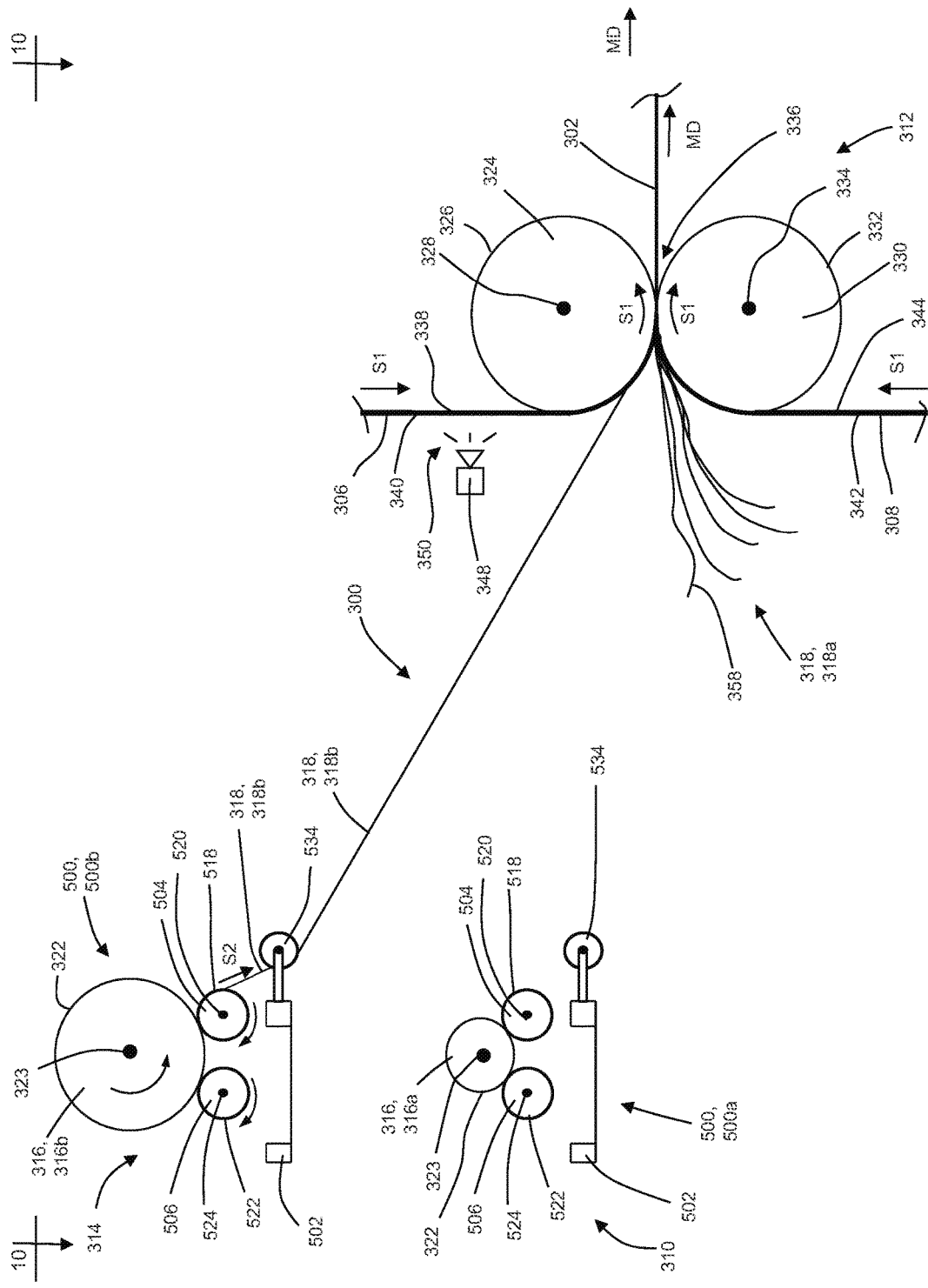
FIG. 9 is a schematic side view of the converting apparatus of FIG. 5 showing the first and second plurality of elastic strands advancing through the nip.
Figure 10:
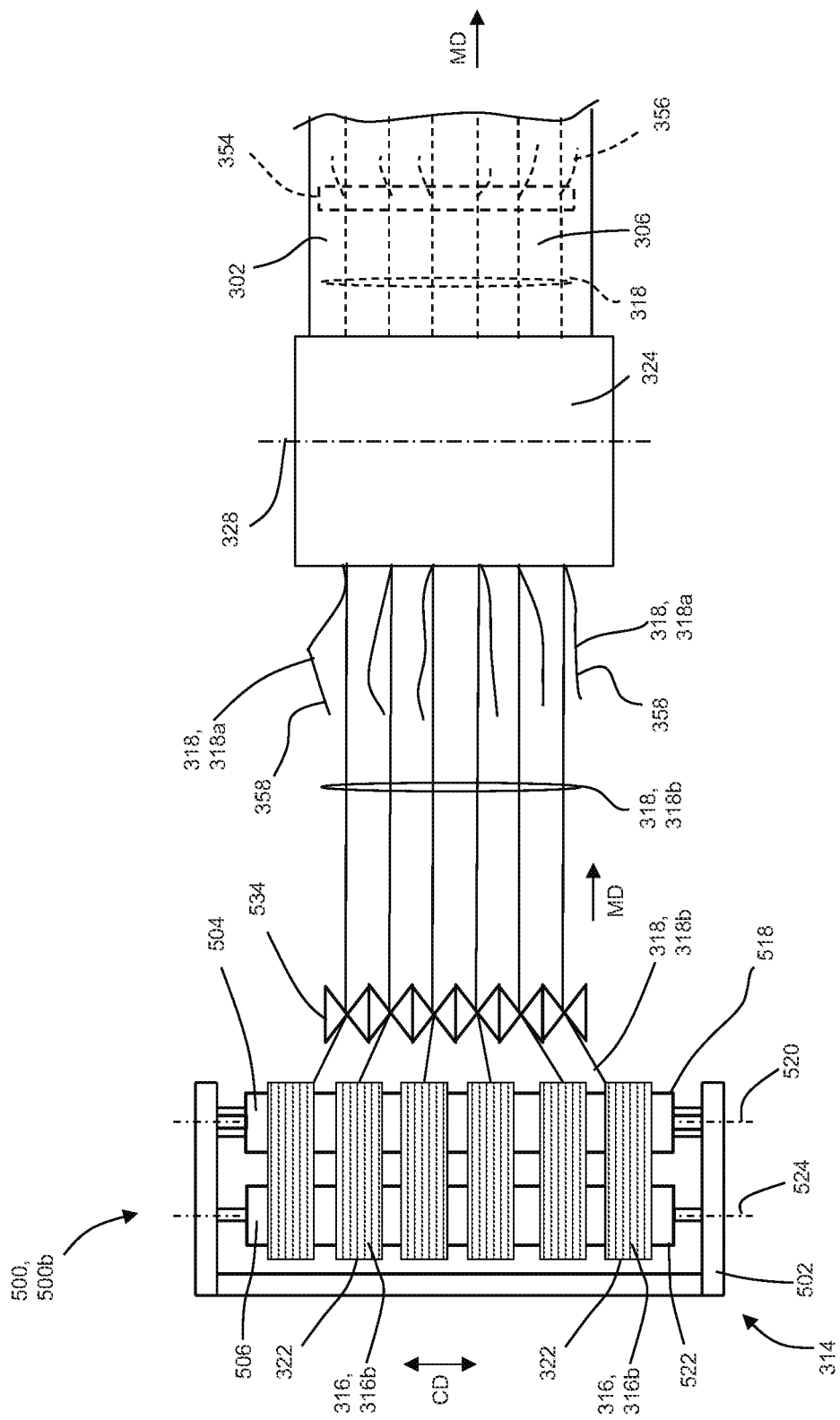
FIG. 10 is a view of the converting apparatus of FIG. 9 taken along line 10-10.

When introducing the second elastic strands 318b into the assembly operation, the second elastic strands 318b may first be connected with a splicer member 354. As shown in FIG. 7, the splicer member 354 may be connected adjacent leading ends 356 of the second elastic strands 318b. In turn, the splicer member 354 and the second elastic strands 318b may be connected with the first elastic strands 318a that are advancing from the first spools 316a on the first unwinder 500a to the nip 336 as shown in FIG. 8. As shown in FIGS. 9 and 10, the splicer member 354 and the leading ends 356 of the second elastic strands 318b advance in the machine direction MD and are positioned between the first and second substrates 306, 308 along with the first elastic strands 318a. Once the second elastic strands 318b are combined with the first substrate 306 and/or second substrate 308, advancement of the first elastic strands 318a from the first spools 316a on the first unwinder 500a may be discontinued. In some instances, advancement of the first elastic strands 318a from the first unwinder 500a may be discontinued as a result of the first elastic strands 318a being completely unwound from the first spools 316a such that trailing ends 358 of the first elastic strands 318a advance through the nip 336 such as shown in FIGS. 9 and 10. In some configurations, the first elastic strands 318a may be cut to discontinue advancement from the first unwinder 500a.

Figure 11:
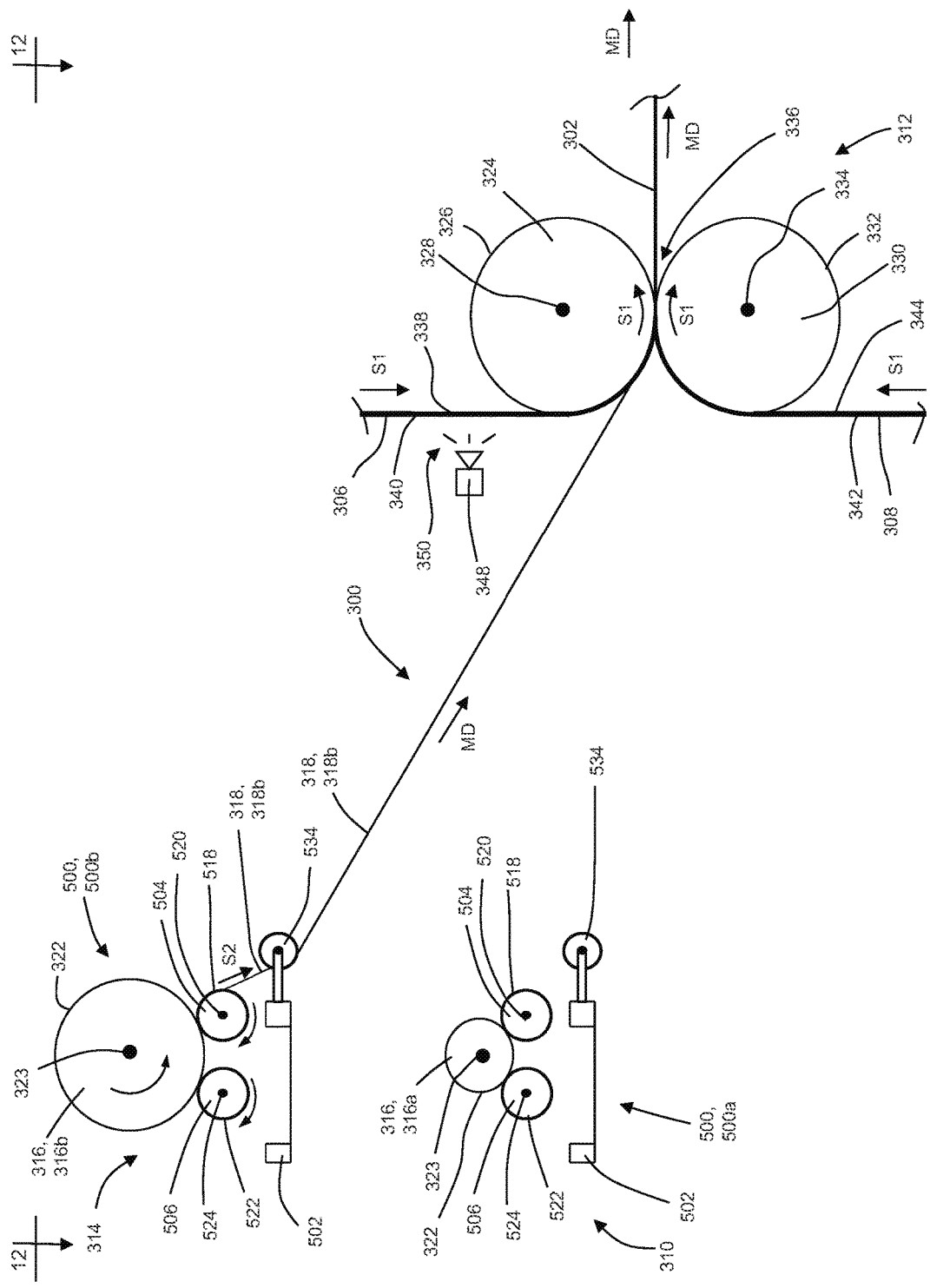
FIG. 11 is a schematic side view of the converting apparatus of FIG. 5 assembling the elastomeric laminate with the second plurality of elastic strands positioned between the first and second substrates.
Figure 12:
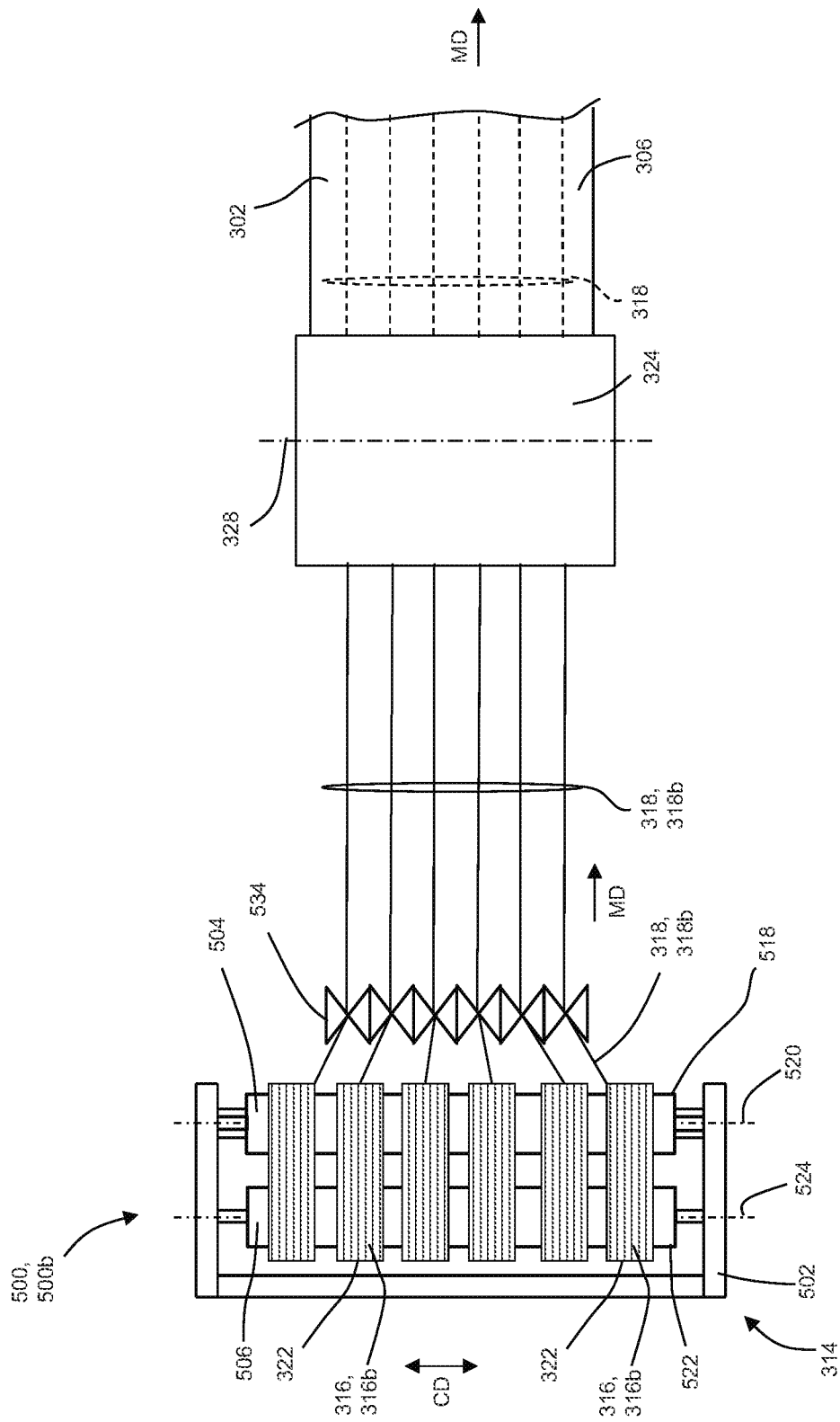
FIG. 12 is a view of the converting apparatus of FIG. 11 taken along line 12-12.

As shown in FIGS. 11 and 12, the apparatus 300 continues to operate to assemble the elastomeric laminate 302 with the second elastic strands 318b unwound from the second spools 316b on the second unwinder 500b. As the second spools 316b rotate, the second elastic strands 318b advance from the second spools 316b at a speed S2 with the second elastic strands 318b being spaced apart from each other in the cross direction CD. From the second unwinder 500b, the second elastic strands 318b advance in the machine direction MD to the nip 336. In some configurations, the speed S2 is less than the speed S1, and as such, the second elastic strands 318b are stretched in the machine direction MD. In turn, the stretched second elastic strands 318b advance through the nip 336 between the first and second substrates 306, 308 such that the second elastic strands 318b are joined with the second surface 340 of the first substrate 306 and the first surface 342 of the second substrate 308 to produce the continuous length of elastomeric laminate 302. Thus, the second plurality of elastic strands 318b can be introduced into the assembly operation as replacements for the first elastic stands 318a without having to stop rotation of the first spools 316a and without having to stop the elastomeric laminate 302 assembly operation. In turn, the empty or depleted first spools 316a on the first unwinder 500a can be replaced with an unwinder 500 with replenished spools 316 with elastic strands 318 wound thereon positioned to replace the second elastics 318b once depleted from the second spools 316b on the second unwinder 500b. It is to be appreciated that an unwinder 500 can be prepared off-line for insertion into an elastomeric laminate 302 assembly operation. For example, several spools 316 may be loaded or positioned onto an unwinder 500, and ends of elastic strands 318 may be partially unwound from the spools 316 and connected with the splicer member 354. The loaded and replenished unwinder 500 can then be placed in an appropriate position adjacent the assembly operation to enable relatively quick splice preparation.

It is to be appreciated that the apparatus 300 can be configured to operate in various ways to advance the leading ends 356 of the second elastic strands 318b between the first and second substrates 306, 308. For example, the splicer member 354 discussed above with reference to FIG. 7 may include one or more tacky surfaces 360 adapted to adhere to the second elastic strands 318b. In addition, the one or more tacky surfaces 360 may also adhere the splicer member 354 with the advancing first elastic strands 318a as described above with reference to FIGS. 8-10. It is also to be appreciated that the splicer member 354 may be connected with the first elastic strands 318a with adhesive applied to the first elastic strands 318a upstream of the nip 336. It is also to be appreciated that in some configurations of the apparatus 300, the second elastic strands 318b may be introduced into the assembly operation without having to connect the second elastic strands 318b with a splicer member 354.

Figure 13:
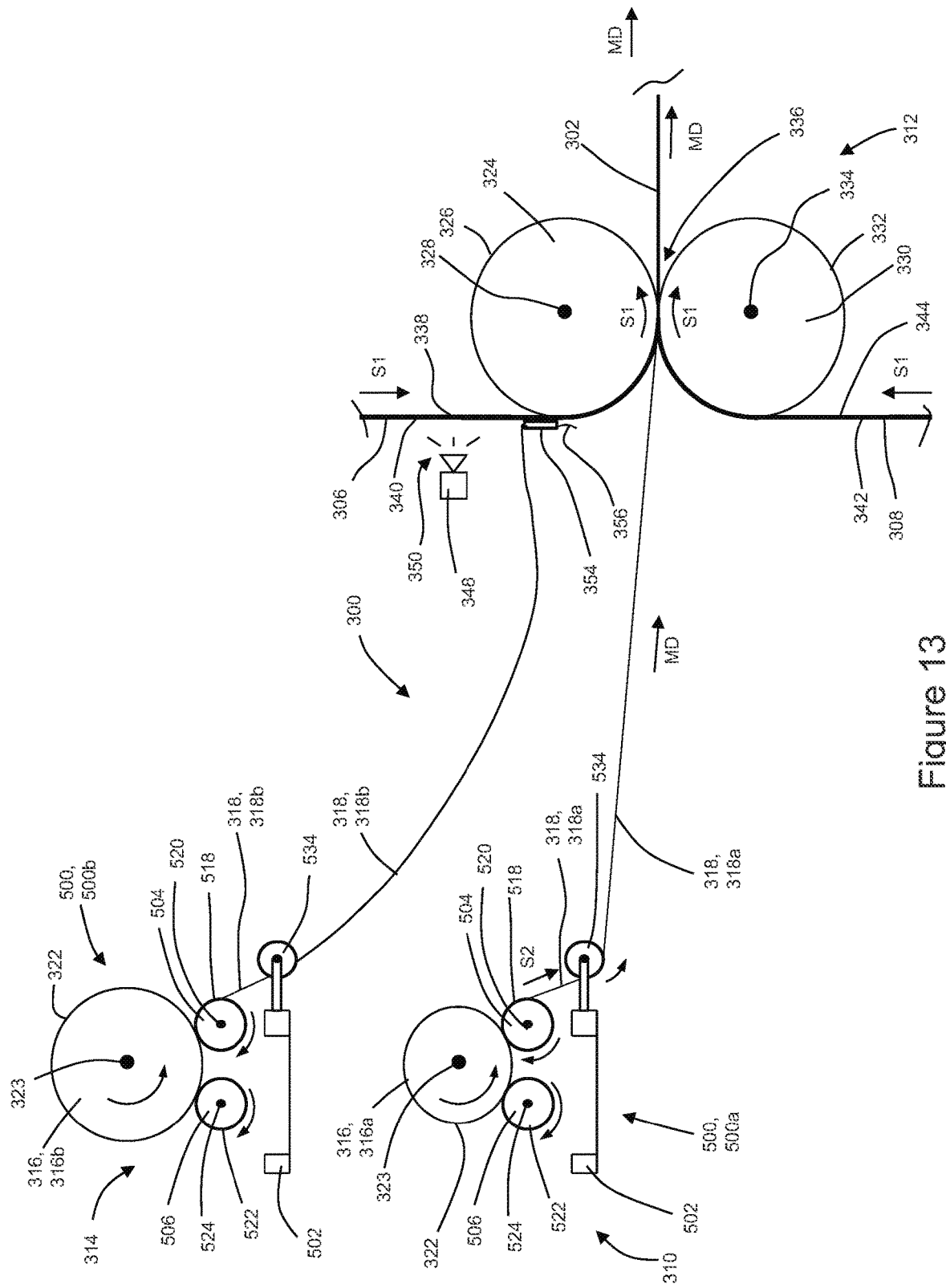
FIG. 13 is a schematic side view of the converting apparatus of FIG. 5 showing the second plurality of elastic strands connected with the first substrate upstream of a nip.

In some configurations, as opposed to being connected with the first elastic strands 318a, the splicer member 354 and/or second elastic strands 318b may be connected with the first substrate 306 or the second substrate 308 upstream of the nip 336. For example, as shown in FIG. 13, after second elastic strands 318b are connected with the splicer member 354, the splicer member 354 may be connected with the second surface 340 of the first substrate 306. As discussed above, the splicer member 354 may include a tacky surface 360 that adheres to the first substrate 306 and/or may be adhered to the first substrate with adhesive 350. Once the splicer member 354 is connected with the first substrate 306, the splicer member 354 and second elastic strands 318b advance along with the first substrate 306 through the nip 336.

It is to be appreciated that different components may be used to construct the elastomeric laminates 302 in accordance with the methods and apparatuses herein. For example, the first and/or second substrates 306, 308 may include nonwovens and/or films. In addition, the first and/or second elastic strands 318a, 318b may be configured in various ways and having various decitex values. In some configurations, the first and/or second plurality of elastic strands 318a, 318b may be configured with decitex values ranging from about 10 decitex to about 500 decitex, specifically reciting all 1 decitex increments within the above-recited range and all ranges formed therein or thereby. It is also to be appreciated the first unwinder 500a and the second unwinder 500b may be configured in various ways and with various quantities of spools 316 of elastic strands 318. Although FIG. 6 shows six spools 316a positioned on the first unwinder 500a and six elastic strands 318a advancing from the first unwinder 500a, it is to be appreciated that the first unwinders 500a herein may be configured with more or less than six spools 316a and more or less than six elastic strands 318a advancing from the first unwinder 500a. And although FIG. 7 shows six spools 316 positioned on the second unwinder 500b and six elastic strands 318 advancing from the second unwinder 500b, it is to be appreciated that the apparatuses herein may be configured with more or less than six spools 316b and more or less than six elastic strands 318b advancing from the second unwinder 500b. In some configurations, the unwinders 500 herein may include from 1 to about 50 spools 316 positioned thereon, and thus, may have from 1 to about 50 elastic strands 318 advancing therefrom, specifically reciting all 1 spool and strand increments within the above-recited range and all ranges formed therein or thereby. It is also to be appreciated that one or more unwinders 500 and spools 316 of elastics 318 positioned thereon may be arranged along the cross direction CD of a converting process and/or arranged along a machine direction MD in various different portions of a converting process.

It is also to be appreciated that the elastic strands 318 advancing from the unwinder 500 may be separated from each other by various distances in the cross direction CD. In some configurations, the first elastic strands 318a and/or the second elastic strands 318b may be separated from each other by about 0.5 mm to about 4 mm in the cross direction, specifically reciting all 0.1 mm increments within the above-recited range and all ranges formed therein or thereby. It is also to be appreciated that the separation distance between the elastic strands 318 advancing the from the unwinder 500 may be changed after the elastic strands 318 advance from the respective spools 316. For example, as shown in FIGS. 6 and 7, the elastic strands 318 may advance from respective spools 316 on the unwinder 500 to a strand guide 534 before advancing to assembly operations downstream. The strand guide 534 may operate to change and/or dictate the cross directional separation distance between the elastic strands 318 advancing the from the unwinder 500. It is to be appreciated that the strand guide 534 may be configured in various ways. For example, as shown in FIGS. 4A-4C, the strand guide 534 may include a plurality of rollers 536. In some configurations, the strand guide 534 may be configured as a comb or a plurality of reeds. As shown in FIGS. 4A-4C, the strand guide 534 may be connected with the frame 502 of the unwinder 500. In some configurations, the strand guide 534 may be a component that is separate from the unwinder 500.

As discussed herein, the elastics in the elastic strands 318 may be pre-strained prior to joining the elastic strands 318 to the first or second substrate layers 306, 308. In some configurations, the elastic may be pre-strained from about 75% to about 300%, specifically reciting all 1% increments within the above-recited range and all ranges formed therein or thereby. Pre-strain refers to the strain imposed on an elastic or elastomeric material prior to combining it with another element of the elastomeric laminate or the absorbent article. Pre-strain is determined by the following equation: Pre-strain=((extended length of the elastic-relaxed length of the elastic)/relaxed length of the elastic)*100.

Figure 14:
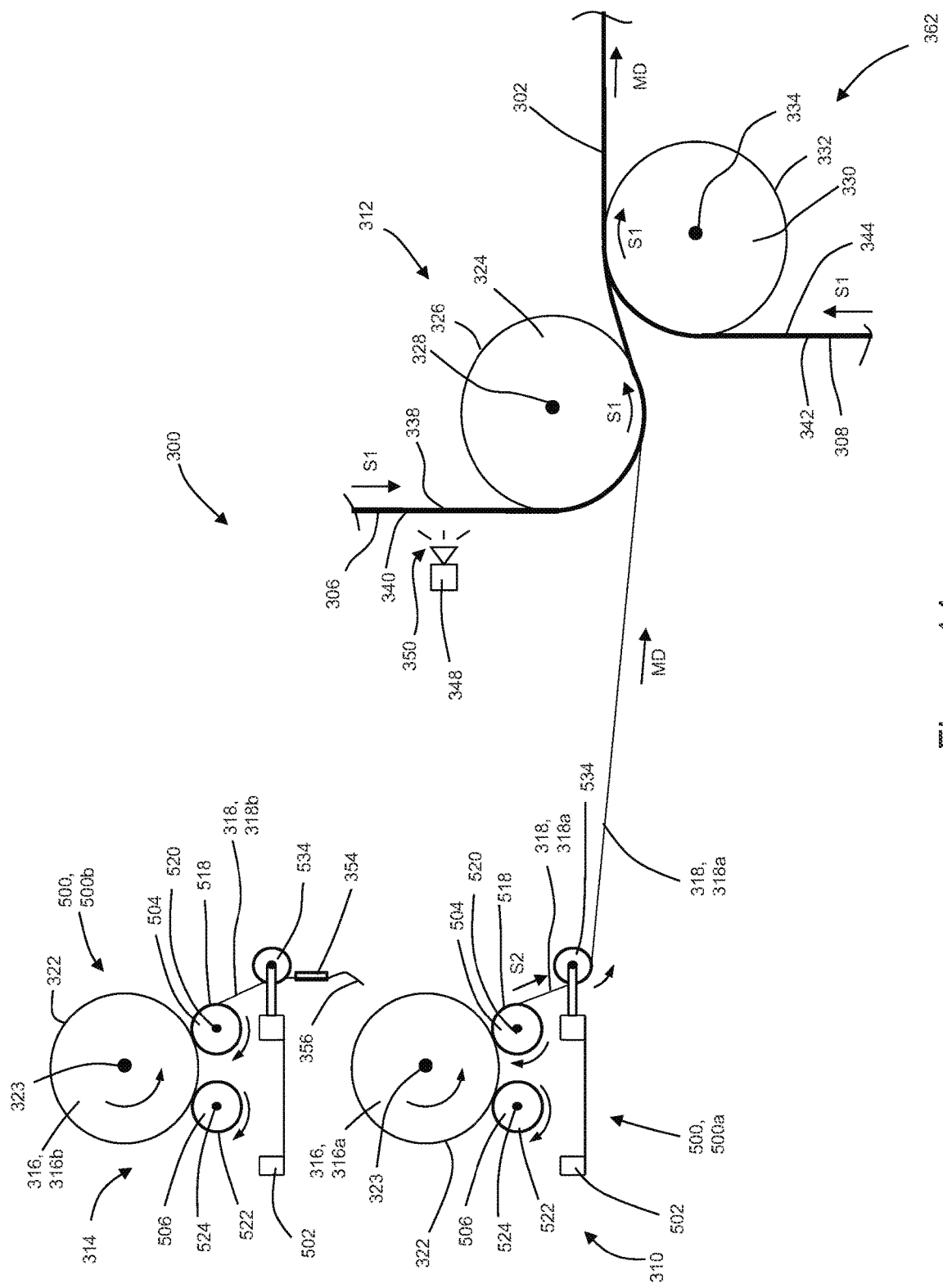
FIG. 14 is a schematic side view of another configuration of a converting apparatus adapted to manufacture an elastomeric laminate including a first plurality of elastic strands positioned between a first substrate and a second substrate.

It is to be appreciated that the apparatuses 300 herein may be configured in various ways. For example, in another configuration of the apparatus 300 shown in FIG. 14, the second roller 330 may be positioned downstream from the first roller 324. As such, the first roller 324 may be configured as the second metering device 312 and the second roller 330 may be configured as a fourth metering device 362. As shown in FIG. 14, the first substrate 306 advances at speed S1 to the first roller 324 where the first substrate 306 partially wraps around the outer circumferential surface 326 of the first roller 324 and advances from the first roller to the second roller 330 to be combined with second substrate 308. As the first roll 504 and the first spools 316a rotate on the first unwinder 500a, the first elastic strands 318a advance from the first unwinder 500a at a speed S2 with the first elastic strands 318a being spaced apart from each other in the cross direction CD. From the first unwinder 500a, the first elastic strands 318a advance in the machine direction MD to the first roller 324 and are positioned on the second surface 340 of the first substrate 306. In some configurations, the speed S2 is less than the speed S1, and as such, the first elastic strands 318a are stretched in the machine direction MD.

With continued reference to FIG. 14, the first substrate 306 and the first elastic strands 318a advance from the outer circumferential surface 326 of the first roller 324 to the second roller 330. In addition, the second substrate 308 advances at speed S1 to the second roller 330 where the second substrate 308 partially wraps around the outer circumferential surface 332 of the second roller 330. In turn, the combined first substrate 306 and the stretched first elastic strands 318a advance from first roller 324 to the second roller 330 and are combined with the second substrate 308 such that the first elastic strands 318a are joined with the second surface 340 of the first substrate 306 and the first surface 342 of the second substrate 308 to produce a continuous length of elastomeric laminate 302. As discussed above, the first substrate 306 may advance past an adhesive applicator device 348 that applies adhesive 350 to the second surface 340 of the first substrate 306 while advancing to the first roller 324. As discussed above, it is to be appreciated that the adhesive 350 may be applied to the first substrate 306 while the first substrate 306 is partially wrapped around the outer circumferential surface 326 of the first roller 324. It is to be appreciated that adhesive may also be applied to the first elastic strands 318 before and/or while being joined with first substrate 306 and second substrate 308. In addition, it is to be appreciated that adhesive may be applied to the first surface 342 of the second substrate 308 before or while being joined with the first elastic strands 318 and first substrate 306. It is also to be appreciated that the elastic strands 318 may be bonded with the first substrate 306 and/or second substrate 308 with various methods and apparatuses, such as described in U.S. Patent Application Nos. 62/436,589; 62/483,965; 62/553,538; 62/553,149; 62/553,171, and 62/581,278 and combinations thereof.

Figure 15:
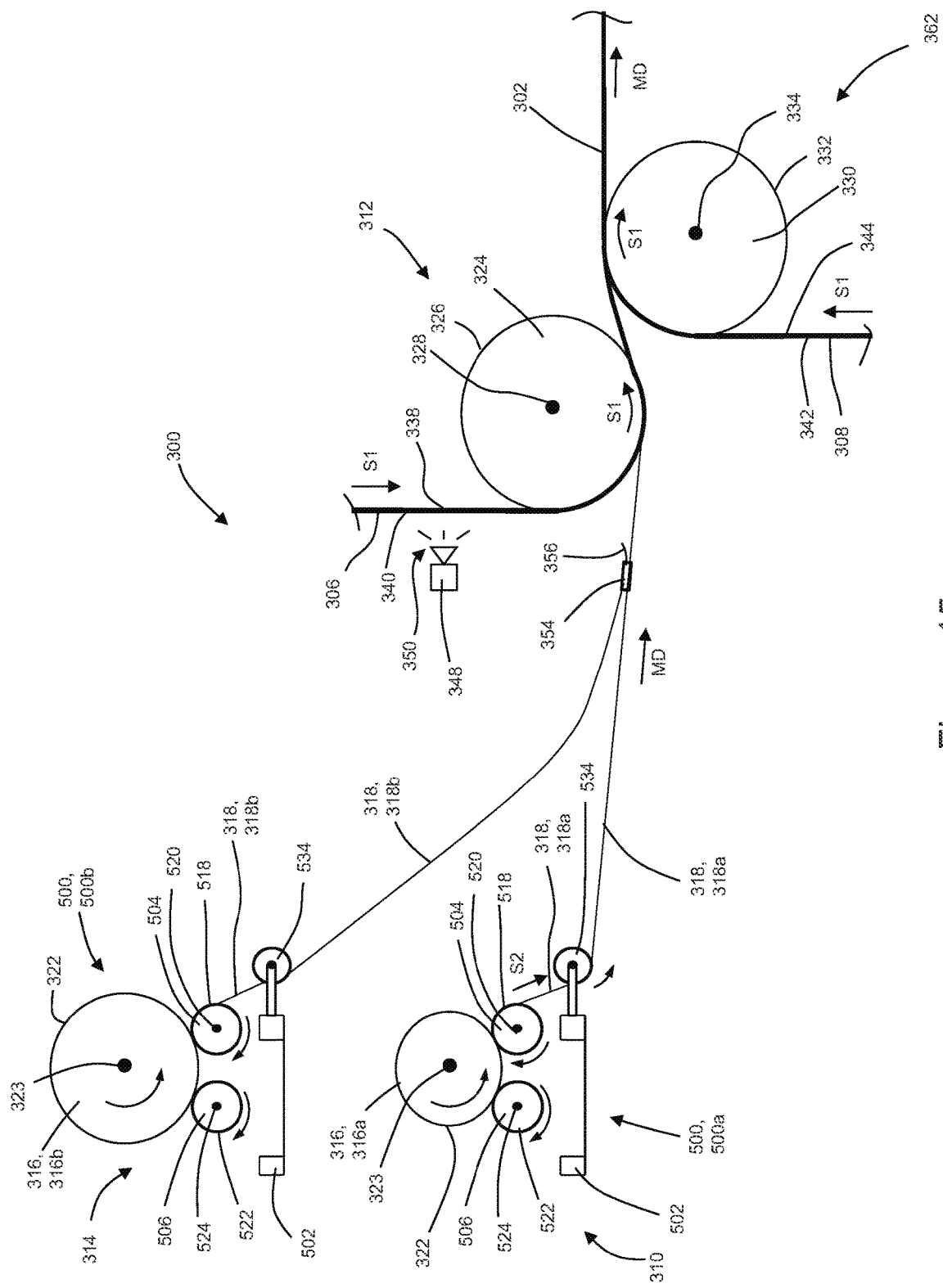
FIG. 15 is a schematic side view of the converting apparatus of FIG. 14 showing a second plurality of elastic strands connected with a first plurality of elastic strands upstream of a first roller.

As previously discussed, the apparatus 300 includes the second elastic strands 318b configured to replace the first elastic stands 318a once the first spools 316a are completely depleted or nearly depleted of first elastic strands 318a. As shown in FIGS. 14 and 15, as the first roll 504 and the second spools 316b rotate on the second unwinder 500b, the second elastic strands 318b advance from the second unwinder 500b at a speed S2 with the second elastic strands 318b being spaced apart from each other in the cross direction CD. As discussed above, the second elastic strands 318b may first be connected with a splicer member 354. In turn, the splicer member 354 and the second elastic strands 318b may be connected with the first elastic strands 318a that are advancing from the first unwinder 500a to the first roller 324, as shown in FIG. 15. As shown in FIG. 15, the splicer member 354 and the leading ends 356 of the second elastic strands 318b advance in the machine direction MD and are positioned on the second surface 340 of the first substrate 306 on the first roller 324. From the first roller 324, the combined first substrate 306, first elastic strands 318, second elastic strands 318b, and splicer member 354 advance to the second roller 330 and are positioned between the first and second substrates 306, 308. Once the second elastic strands 318b are combined with the first substrate 306 and/or second substrate 308, advancement of the first elastic strands 318a from the first unwinder 500a may be discontinued wherein trailing ends 358 of the first elastic strands 318a advance downstream to the first and second rollers 324, 330, such as shown in FIG. 16.

Figure 16:
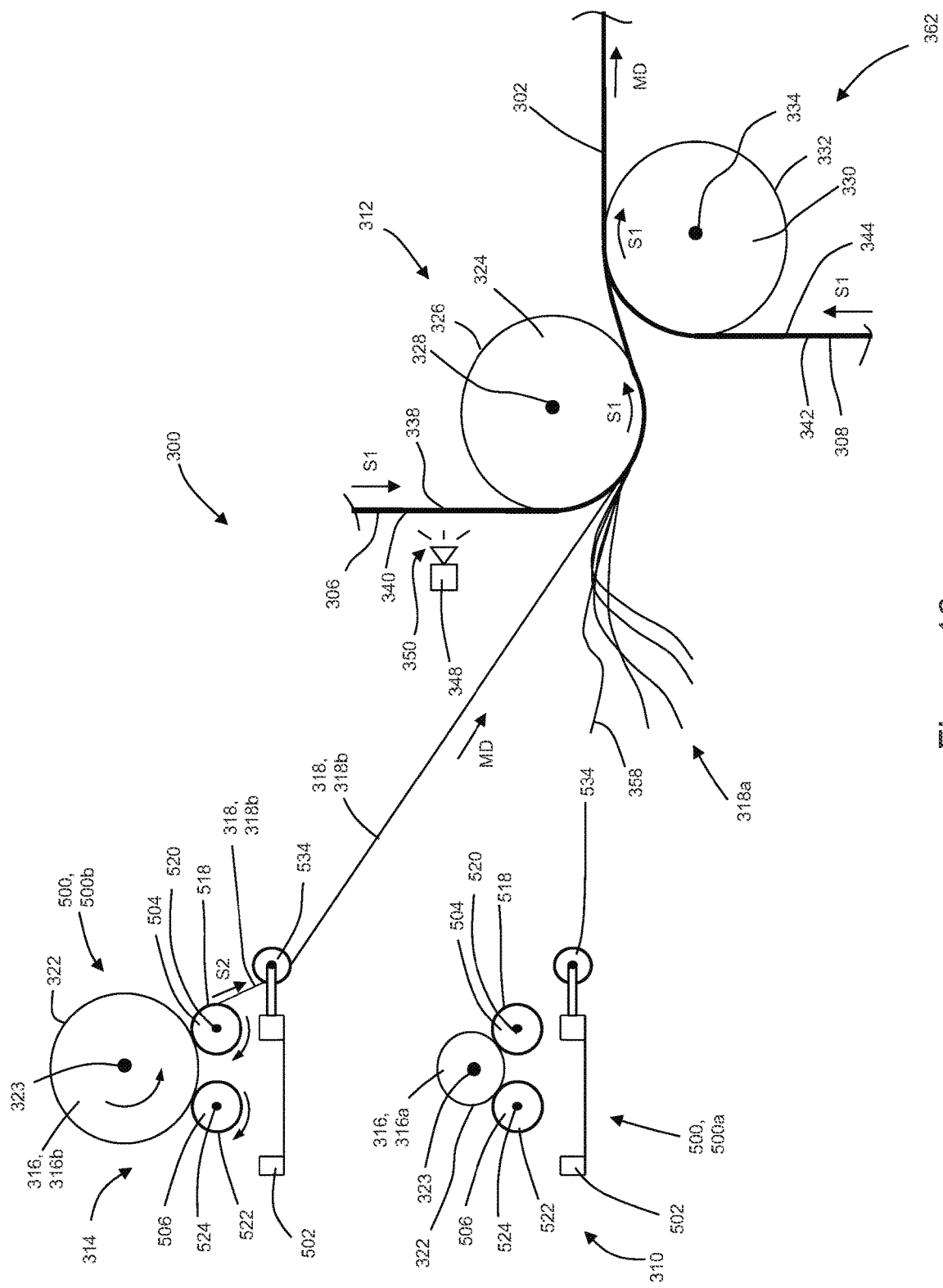
FIG. 16 is a schematic side view of the converting apparatus of FIG. 14 showing the first and second plurality of elastic strands advancing onto the first substrate.
Figure 17:
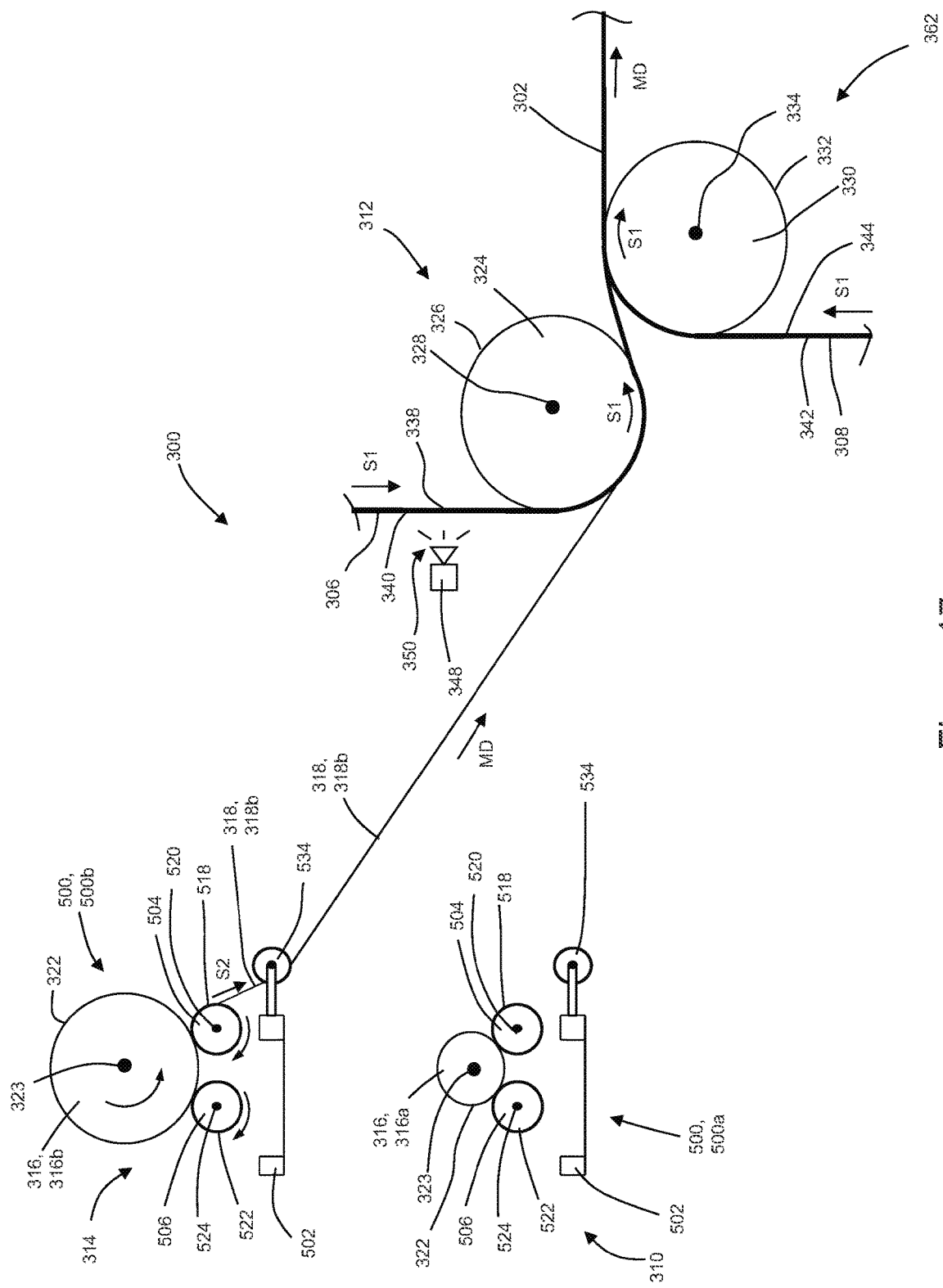
FIG. 17 is a schematic side view of the converting apparatus of FIG. 14 assembling the elastomeric laminate with the second plurality of elastic strands positioned between the first and second substrates.
Figure 18:
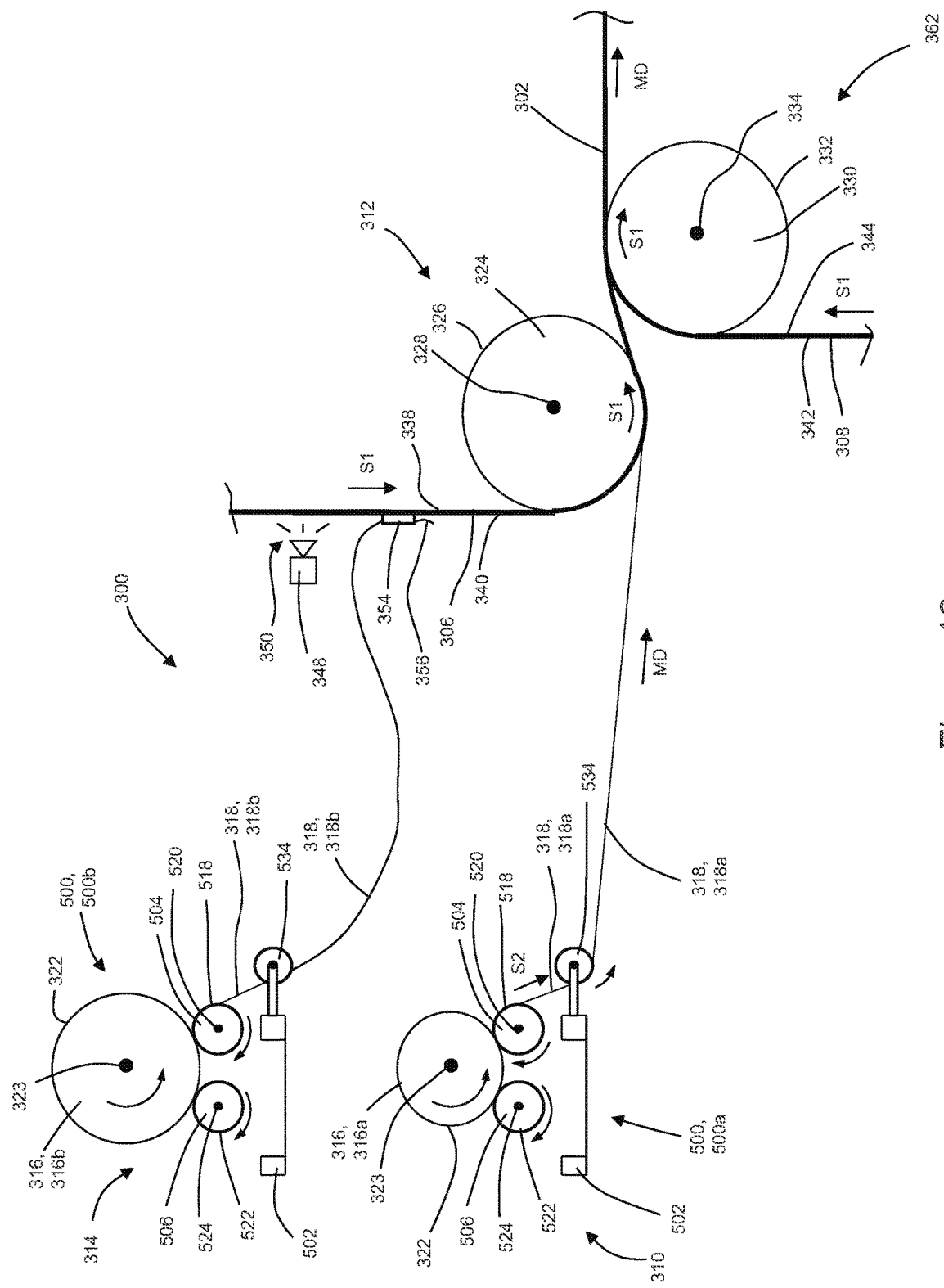
FIG. 18 is a schematic side view of the converting apparatus of FIG. 14 showing the second plurality of elastic strands connected with the first substrate upstream of the first roller.

As shown in FIGS. 16 and 17, the apparatus 300 continues to operate to assemble the elastomeric laminate 302 with the second elastic strands 318b advancing from the second unwinder 500b. As the first roll 504 and the second spools 316b rotate on the second unwinder 500b, the second elastic strands 318b advance from the second unwinder 500b at a speed S2 with the second elastics strands 318b being spaced apart from each other in the cross direction CD. From the second unwinder 500b, the second elastic strands 318b advance in the machine direction MD to the first roller 324 and are positioned on the second surface 340 of the first substrate 306. In some configurations, the speed S2 is less than the speed S1, and as such, the second elastic strands 318b are stretched in the machine direction MD. In turn, the stretched second elastic strands 318b advance from the first roller 324 to the second roller 330 such that the second elastic strands 318b are joined with the second surface 340 of the first substrate 306 and the first surface 342 of the second substrate 308 to produce the continuous length of elastomeric laminate 302.

As discussed above and as shown in FIG. 18, as opposed to being connected with the first elastic strands 318, the splicer member 354 and the second elastic strands 318b may be connected with the first substrate 306 upstream of the first roller 306. Once the splicer member 354 is connected with the first substrate 306, the splicer member 354 and second elastic strands 318b advance along with the first substrate 306 to the first roller 306 and the second roller 330 to assemble the elastomeric laminate 302.

As previously mentioned, the second elastic strands 318b may be introduced into the assembly operation without having to connect the second elastic strands 318b with a splicer member 354. Thus, the second elastic strands 318b may be connected directly with the first substrate 306. It is also to be appreciated that the splicer member 354 and/or the second elastic strands 318b may be connected with the first substrate 306 while partially wrapped around the outer circumferential surface 326 of the first roller 306. It is also to be appreciated that the splicer member 354 and/or the second elastic strands 318b may be connected with the second substrate 308 upstream of the second roller 330 or while partially wrapped around the outer circumferential surface 332 of the second roller 330.

Figure 19:
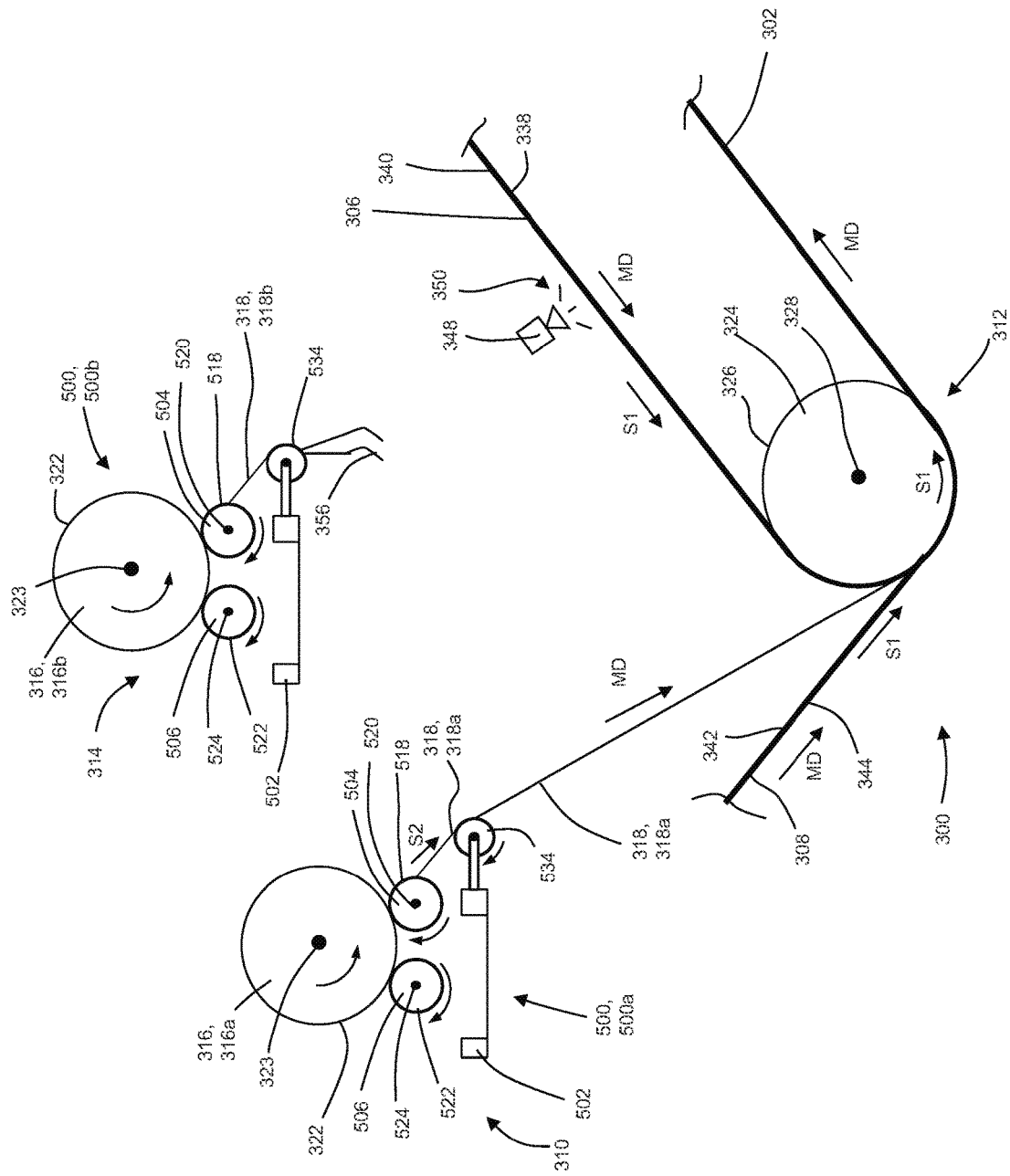
FIG. 19 is a schematic side view of another configuration of a converting apparatus adapted to manufacture an elastomeric laminate including a first plurality of elastic strands positioned between a first substrate and a second substrate.

In another configuration shown in FIG. 19, the apparatus 300 may be configured with only the first roller 324 and without a second roller 330. As such, the first roller 324 may be configured as the second metering device 312. As shown in FIG. 19, the first substrate 306 advances at speed S1 to the first roller 324 where the first substrate 306 partially wraps around the outer circumferential surface 326 of the first roller 324. While partially wrapped around the outer circumferential surface 326 of the first roller 324, the first substrate 306 is combined with the first elastic strands 318a and the second substrate 308. As the first roll 504 and the first spools 316a rotate on the first unwinder 500a, the first elastic strands 318a advance from the first unwinder 500a at a speed S2 with the first elastic strands 318a being spaced apart from each other in the cross direction CD. From the first unwinder 500a, the first elastic strands 318a advance in the machine direction MD to the first roller 324 and are positioned on the second surface 340 of the first substrate 306. In some configurations, the speed S2 is less than the speed S1, and as such, the first elastic strands 318a are stretched in the machine direction MD.

With continued reference to FIG. 19, the second substrate 308 advances at speed S1 to the first roller 324 and partially wraps around the outer circumferential surface 326 of the first roller 324. In turn, the second substrate 308 is combined with the first substrate 306 and the stretched first elastic strands 318a while on the first roller 324 such that the first elastic strands 318a are joined with the second surface 340 of the first substrate 306 and the first surface 342 of the second substrate 308 to produce a continuous length of elastomeric laminate 302. As discussed above, the first substrate 306 may advance past an adhesive applicator device 348 that applies adhesive 350 to the second surface 340 of the first substrate 306 while advancing to the first roller 324. It is to be appreciated that the adhesive 350 may be applied to the first substrate 306 while the first substrate 306 is partially wrapped around the outer circumferential surface 326 of the first roller 324. It is to be appreciated that adhesive may also be applied to the first elastic strands 318a before and/or while being joined with first substrate 306 and second substrate 308. In addition, it is to be appreciated that adhesive may be applied to the first surface 342 of the second substrate 308 before or while being joined with the first elastic strands 318a and first substrate 306. It is also to be appreciated that the elastic strands 318 may be bonded with the first substrate 306 and/or second substrate 308 with various methods and apparatuses, such as described in U.S. Patent Application Nos. 62/436,589; 62/483,965; 62/553,538; 62/553,149, 62/553,171, and 62/581,278 and combinations thereof.

Figure 20:
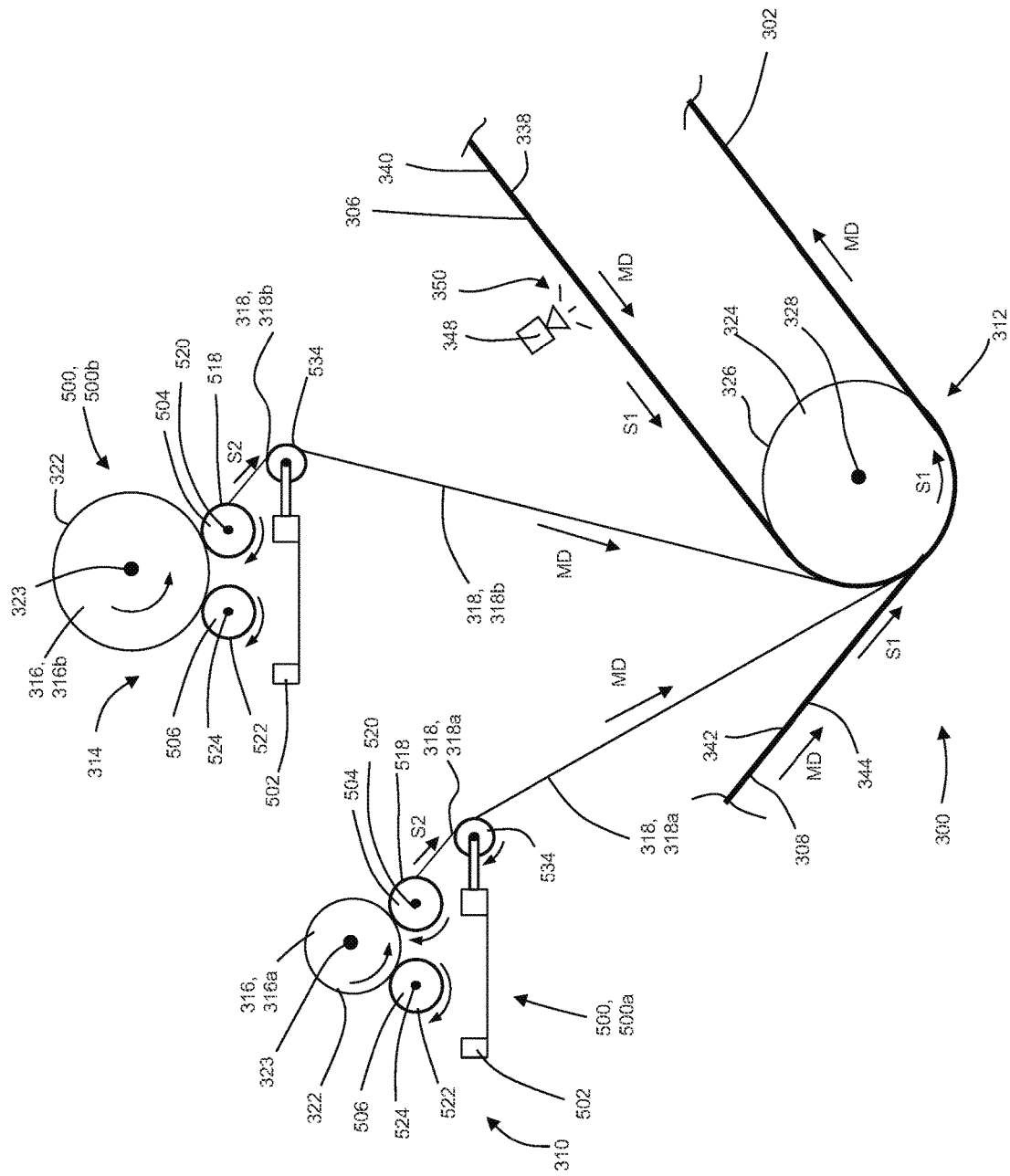
FIG. 20 is a schematic side view of the converting apparatus of FIG. 19 assembling the elastomeric laminate with the first and second plurality of elastic strands advancing between the first and second substrates.

As previously discussed, the apparatus 300 includes the second elastic strands 318b configured to replace the first elastic stands 318a once the first spools 316a are completely depleted or nearly depleted of first elastic strands 318a. As shown in FIGS. 19 and 20, as the first roll 504 and the second spools 316b rotate on the second unwinder 500b, the second elastic strands 318b advance from the second unwinder 500b at a speed S2 with the second elastic strands 318b being spaced apart from each other in the cross direction CD. In turn, leading ends 356 of the second plurality of elastic strands 318b may be advanced onto the first roller 324 and between first substrate 306 and the second substrate 308. As such, the second elastic strands 318b are positioned in between the second surface 340 of the first substrate 306 and the first surface 342 of the second substrate 308 such that the first elastic strands 318a, the second elastic strands 318b, and the first substrate 306 are positioned between the second substrate 308 and the outer circumferential surface 326 of the first roller 324. As discussed above, the second elastic strands 318b may also be first connected with a splicer member 354. Thus, it is to be appreciated that the splicer member 354 and/or the second elastic strands 318b may be connected with the first elastic strands 318a, the first substrate 306, or the second substrate 308. As shown in FIGS. 19 and 20, the leading ends 356 of the second elastic strands 318b advance in the machine direction MD and are positioned on the second surface 340 of the first substrate 306 on the first roller 324. And the second substrate 306 advances to the first roller 324 to be combined with first substrate 306, first elastic strands 318a, and second elastic strands 318b to form the elastomeric laminate 302. Once the second elastic strands 318b are combined with the first substrate 306 and/or second substrate 308, advancement of the first elastic strands 318a from the first unwinder 500a may be discontinued wherein trailing ends 358 of the first elastic strands 318a advance downstream to the first roller 324, such as shown in FIG. 21.

Figure 21:
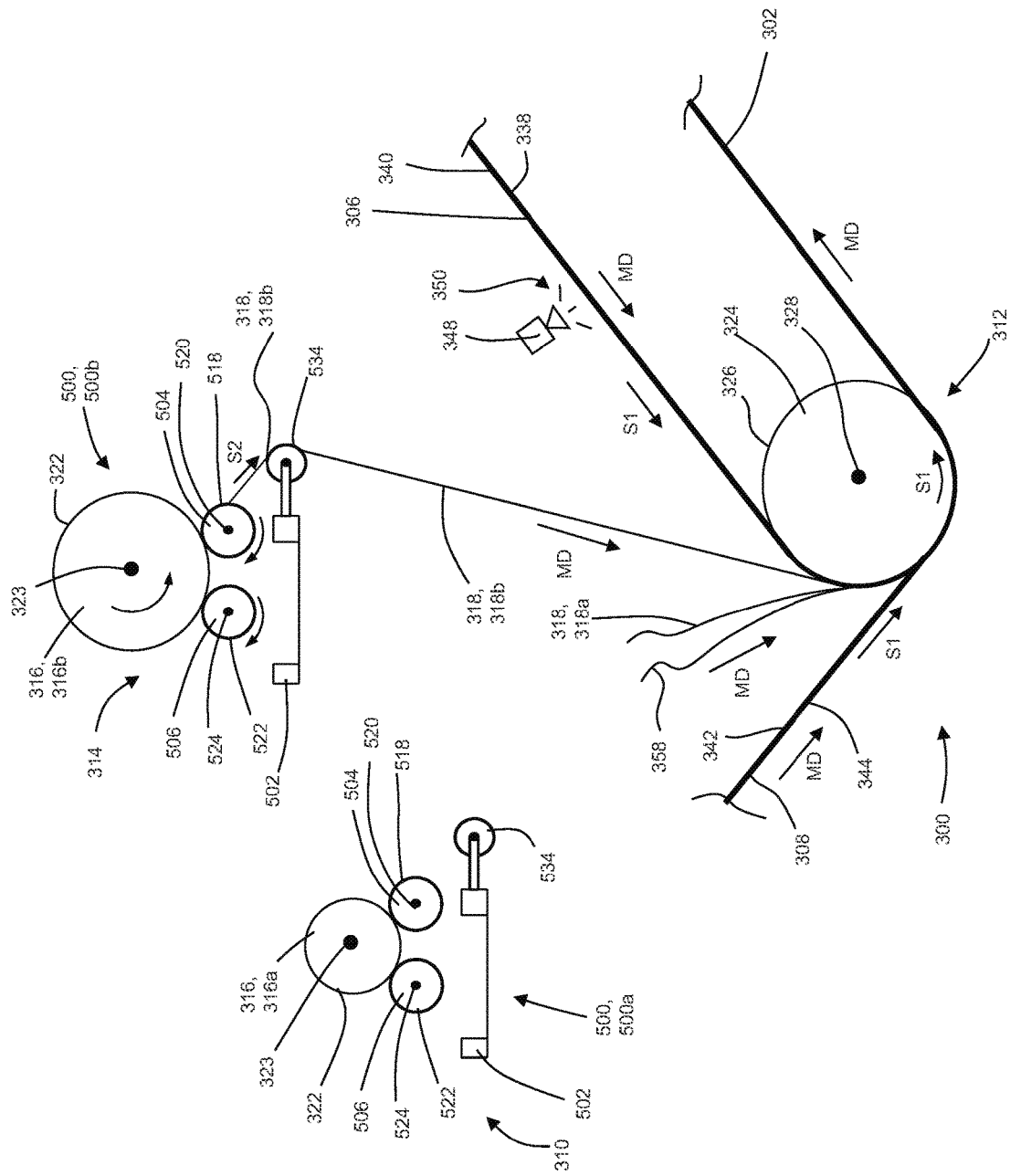
FIG. 21 is a schematic side view of the converting apparatus of FIG. 19 assembling the elastomeric laminate showing the trailing ends of the first plurality of elastic strands advancing between the first and second substrates.
Figure 22:
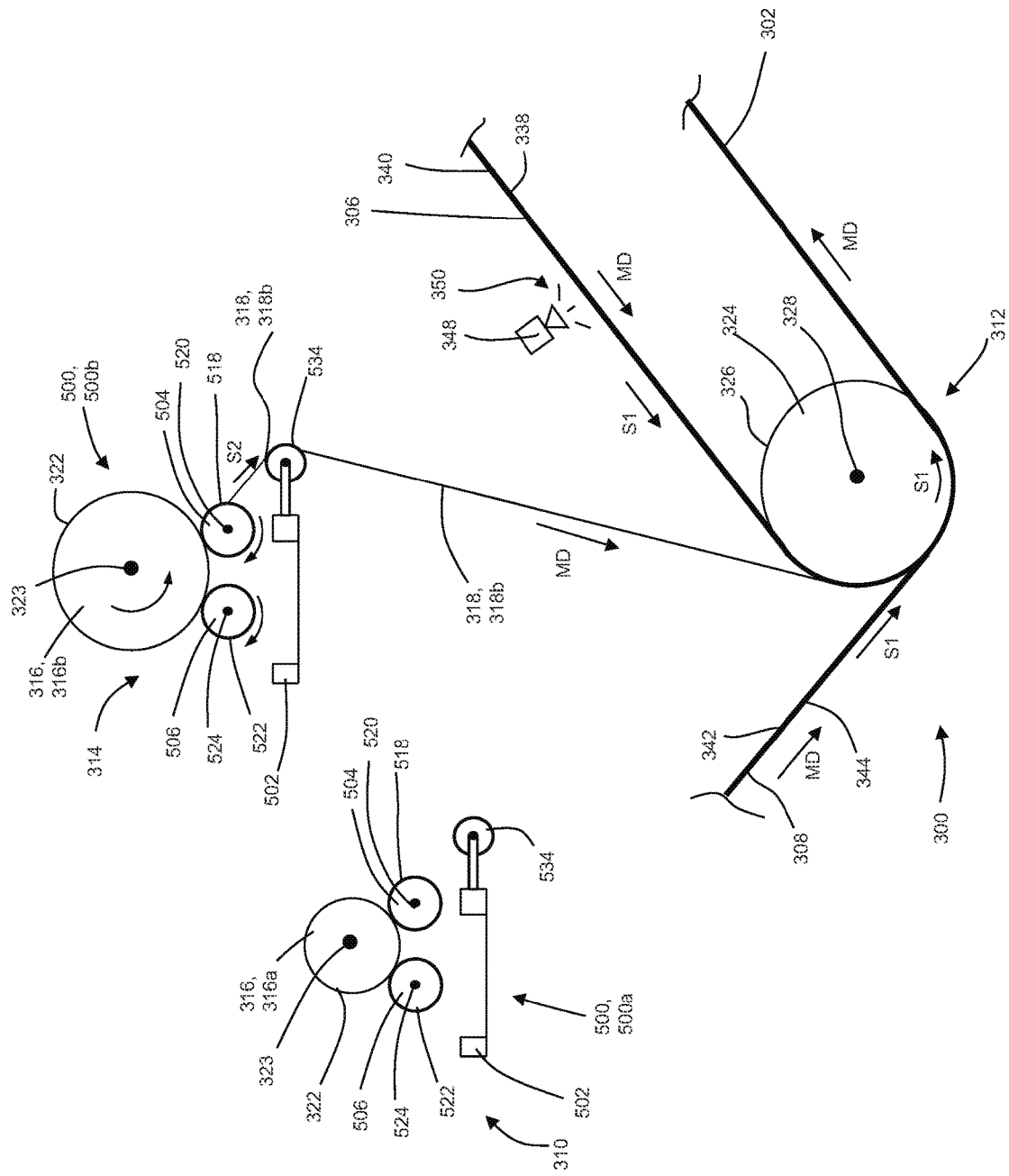
FIG. 22 is a schematic side view of the converting apparatus of FIG. 19 assembling the elastomeric laminate with the second plurality of elastic strands positioned between the first and second substrates.

As shown in FIGS. 21 and 22, the apparatus 300 continues to operate to assemble the elastomeric laminate 302 with the second elastic strands 318b advancing from the second unwinder 500b. As the first roll 504 and the second spools 316b rotate on the second unwinder 500b, the second elastic strands 318b advance from the second unwinder 500b at a speed S2 with the second elastic strands 318b being spaced apart from each other in the cross direction CD. From the second unwinder 500b, the second elastic strands 318b advances in the machine direction MD to the first roller 324 and are positioned on the second surface 340 of the first substrate 306. In some configurations, the speed S2 is less than the speed S1, and as such, the second elastic strands 318b are stretched in the machine direction MD. In turn, the stretched second elastic strands 318b are joined with the second surface 340 of the first substrate 306 and the first surface 342 of the second substrate 308 to produce the continuous length of elastomeric laminate 302 that advances from the first roller 324.

It is to be appreciated that in the various process configurations discussed above, the second elastic strands 318b may be first connected with a splicer member 354 before advancing the elastic strands 318b in the assembly process. It is also to be appreciated that in the various process configurations discussed above, the second elastic strands 318b may be advanced directly into the assembly process without connecting the stands 318b to a splicer member. In some configurations, the second elastic strands 318b may be connected or tied to each other with a knot before advancing into the assembly process. In some configurations, the first substrate 306 and/or second substrate 308 may have an electrostatic charge that attracts the elastic strands 318b to the substrates 306, 308 before advancing into assembly process. Further, in some configurations, the elastic strands 318b may be directed into the assembly process by air flow, such as provided from a fan and/or a vacuum system.

Figure 23:
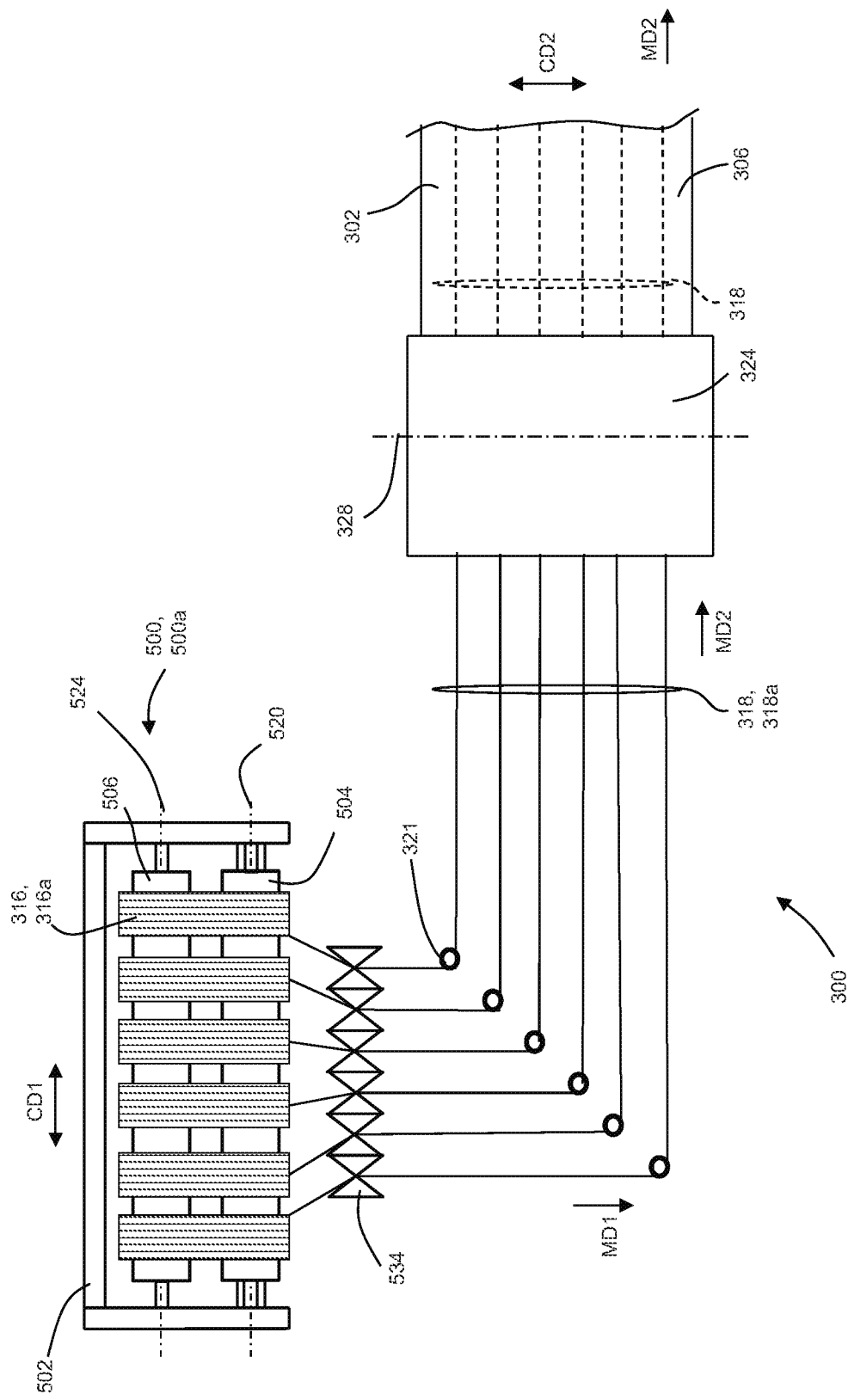
FIG. 23 is a schematic side view of a converting apparatus adapted to manufacture an elastomeric laminate.

It is to be appreciated that the apparatuses and processes may be configured such that elastic strands may be advanced from the unwinders 500 and directly to the assembly process without having to touch additional machine components, such as for example, guide rollers. It is also to be appreciated that in some configurations, elastic strands may be advanced from the unwinders and may be redirected and/or otherwise touched by and/or redirected before advancing to the assembly process. For example, FIG. 23 shows a configuration where the rotation axis 520 of the first roll 504 of the first unwinder 500a may extend in a first cross direction CD1. As the first roll 504 and first spools 316a rotate, the first elastic strands 318a advance from the first unwinder 500a in a first machine direction MD1 with the first elastic strands 318a being spaced apart from each other in the first cross direction CD1. The first elastic strands 318a may then be redirected by rollers 321 from the first machine direction MD1 to a second machine direction MD2, wherein the first elastic strands 318a may remain separated from each other in a second cross direction CD2. From the rollers 321, the first elastic strands 318a may advance in the second machine direction MD2 to be combined with the first and second substrates 306, 308 to form the elastic laminate 302. Thus, it is to be appreciated that the first and/or second unwinders 500a, 500b and associated spools 316a, 316b may be arranged and/or oriented such that the rotation axis 520 of the first rolls 504 and/or rotation axes 323 of spools 316a, 316b may be parallel, perpendicular, or otherwise angularly offset with respect to the machine direction advancement of the elastic laminate 302 and/or the substrates 306, 308.

Although FIGS. 4A-23 illustrate unwinders 500 configured as surface unwinders in that the spools 316 may be driven by the first roll 504 or the second roll 506 in contact with the outer circumferential surfaces 322 of the spools 316, it is to be appreciated that the unwinders 500 herein may be configured in different ways. For example, the unwinders 500 shown in FIGS. 5-23 may also be configured as mandrel driven unwinders, such as shown in FIGS. 24A-24E.

Figure 24B:
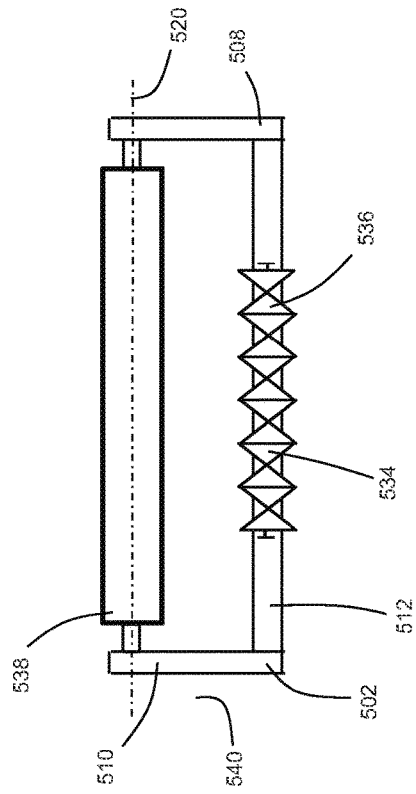
FIG. 24B is a front side view of the unwinder from FIG. 24A taken along line 24B-24B.
Figure 24C:
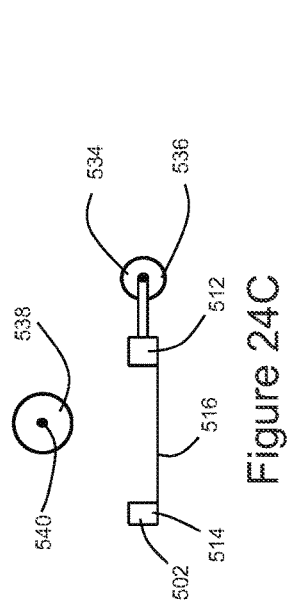
FIG. 24C is a left side view of the unwinder from FIG. 24A taken along line 24C-24C.
Figure 24A:
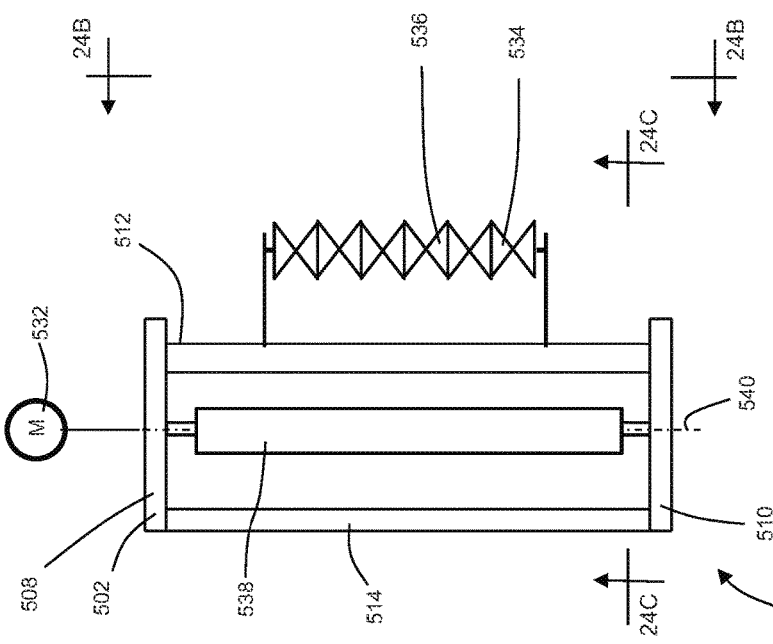
FIG. 24A is a top side view of another configuration of an unwinder.

FIGS. 24A-24C show an example of an unwinder 500 that may include a mandrel 538 rotatably connected with a frame 502. It is to be appreciated that the frame 502 may be configured in various ways, such as described above with reference to FIGS. 4A-4C. With continued reference to FIGS. 24A-24C, the mandrel 538 may be rotatably connected with the first side 508 and the second side 510 of the frame 502, and may be adapted to rotate about a mandrel rotation axis 540.

As shown in FIGS. 24D and 24E, one or more spools 316 may be positioned on and supported by the mandrel 538 of the unwinder 500. More particularly, the cores 320 of one or more spools 316 may be adapted to receive and connect with the mandrel 538. As such, the spools 316 and the mandrel 538 rotate together. It is to be appreciated that the mandrel 538 may be configured to drive and cause rotation of the spools 316. For example, FIG. 24A shows the mandrel 538 connected with a rotation driver 532, such as a motor or a servo motor, to drive and control the rotation of the mandrel 538. During operation, each spool 316 and the mandrel 538 are rotated in the same direction. The elastic strand 318 advances from the rotating spool 316 to downstream assembly operations, such as described herein. The unwinder 500 may also be configured such that the elastic strands 318 advance from the spools 316 at a speed S2 as described above. As elastic strands 318 are drawn from the rotating spools 316 supported on the mandrel 538, the outer diameter of the spools 316 become smaller. In turn, as the outer diameter of the spools 316 become smaller, the rotational speed of the mandrel 538 and spools 316 will need to increase in order to maintain a constant speed S2 of the elastic strands 318 advancing from the spools 316. As such, the apparatus 300 herein may include a sensor 542 that detects the diameter of the spools 316, wherein feedback from the sensor 542 can be used to control the speed of the rotation driver 532 and mandrel 538 to maintain a constant speed S2. In some configurations, the sensor 542 may be configured to detect the tension in the elastic strands 318, wherein feedback from the sensor 542 can be used to control the speed of the rotation driver 532 and mandrel 538 to maintain a constant tension.

It is to be appreciated that the unwinder 500 discussed above with reference to FIGS. 24A-24E can also be prepared off-line for insertion into an elastomeric laminate 302 assembly operation. For example, several spools 316 may be loaded or positioned onto the mandrel 538 of the unwinder 500, and ends of elastic strands 318 may be partially unwound from the spools 316 and connected with the splicer member 354. As discussed with the unwinders above, the loaded and replenished unwinder 500 can then be placed in an appropriate position adjacent the assembly operation to enable relatively quick splice preparation.

It is to be appreciated that a control system and/or an inspection system may be utilized to control various aspects of the splicing operations discussed herein. For example, as previously mentioned, the first roll 504 and/or the second roll 506 of the unwinder 500 may be connected with one or more motors, such as servo motors, to drive and control the rotation of the spools 316. As such, a control system may operate to control the acceleration and/or deceleration of the spools 316 during the splicing operation to achieve and/or maintain the desired tension in the elastic strands 318. In some configurations, the elastic strands 318 may be advanced from the unwinders 500 through a series of dancer rolls to help maintain desired tensions in the elastic strands 318 during splicing operations. As previously mentioned, the elastomeric laminate 302 may also be subject to additional converting processes. Such additional converting processes may incorporate the elastomeric laminate 302 into discrete absorbent articles 100. As such, in some embodiments, an inspection system may be configured to detect and/or track a defective length of the elastomeric laminate 302. With reference to FIG. 10, a defective length of elastomeric laminate 302 may be defined by a length of elastomeric laminate 302 that includes both the first elastic strands 318a and the second elastic strands 318b positioned together between the first and second substrates 306, 308. A defective length of elastomeric laminate 302 may also be defined by a length of elastomeric laminate 302 that includes the splicer member 354, leading ends 356 of the second elastic strands 318b, and/or the trailing ends 358 of the first elastic strands 318a. The inspection system may also correlate inspection results and measurements from the defect length of the elastomeric laminate 302 with absorbent articles 100 made therefrom. In turn, the inspection system may be used to control a reject system on a converting process of absorbent articles, wherein absorbent articles manufactured with portions of the defective length of elastomeric laminate 302 are rejected. In some configurations, defective articles may be subject to the rejection system and removed from the assembly process. Absorbent articles 100 that are not deemed to be defective may be subject to further processing steps, such as folding and packaging. In some configurations, an inspection system may be configured to detect a broken elastic strand advancing from a first unwinder 500a. Upon detection of a broken elastic strand, the inspection system may activate a splicing operation, such as described above, to place a second unwinder 500b into service and remove the first unwinder 500a from service. In some configurations, an inspection and/or a control system may operate to control the timing and placement of the splicer member 354 into the assembly operation, such as in the nip 336 shown in FIG. 5, which may help an inspection system to more accurately track a splicing event. It is to be appreciated that such an inspection system may be configured in various ways, such as disclosed in U.S. Patent Publication No. 2013/0199696 A1.

It is to be appreciated that the apparatuses 300 herein may be configured in various ways with various features described herein to assemble elastomeric laminates 302 having various stretch characteristics. For example, the apparatus 300 may be configured to assemble elastomeric laminates 302 with elastic strands 318 unwound from more than one unwinder 500 and/or in combination with elastic stands supplied from various types of elastic unwinder configurations, such as an overend unwinder and/or beams (also referred to as warp beams), such as disclosed in U.S. Pat. Nos. 6,676,054; 7,878,447; 7,905,446; 9,156,648; 4,525,905; 5,060,881; and 5,775,380; and U.S. Patent Publication No. 2004/0219854 A1. Additional examples of beam elastics and associated handling equipment are available from Karl Mayer Corporation.

In some configurations, the elastic strands 318 may be joined with the first and second substrates 306, 308 such that the elastomeric laminate 302 may have different stretch characteristics in different regions along the cross direction CD, such as disclosed in U.S. Patent Application Nos. 62/436,589; 62/483,965; 62/553,538; 62/553,149; 62/553, 171; 62/581,278; and Ser. No. 15/839,896, which are all incorporated by reference herein. For example, when the elastomeric laminate 302 is elongated, some elastic strands may exert contraction forces in the machine direction MD that are different from contraction forces exerted by other elastic strands 318. Such differential stretch characteristics can be achieved by stretching some elastic strands 318 more or less than other elastic strands 318 before joining the elastic strands with the first and second substrates 306, 308. It is also to be appreciated that the elastic strands 318 may have various different material constructions and/or decitex values to create elastomeric laminates 302 having different stretch characteristics in different regions. In some configurations, the spools 316 of elastic strands 318 having different decitex values may be positioned on and advanced from an unwinder 500. In some configurations, the elastomeric laminate 302 may have regions where the elastic strands 318 are spaced relatively close to one another in the cross direction CD and other regions where the elastic strands 318 are spaced relatively far apart from each other in the cross direction CD to create different stretch characteristics in different regions. In some configurations, the elastic strands 318 may be supplied on the spool 316 in a stretched state, and as such, may not require additional stretching (or may require relatively less additional stretching) before being combined with the first substrate 306 and/or the second substrate 308. In some configurations, differential stretch characteristics in an elastomeric laminate may be created by bonding another elastomeric laminate and/or an elastic film to a particular region of an elastomeric laminate. In some configurations, differential stretch characteristics in an elastomeric laminate may be created by folding a portion of an elastomeric laminate onto itself in a particular region of the elastomeric laminate.

It is to be appreciated the elastic strands 318 may include various types of spin finish, also referred herein as yarn finish, configured as coating on the elastic strands 318 that may be intended to help prevent the elastics strands from adhering to themselves, each other, and/or downstream handling equipment. In some configurations, a spin finish may include various types of oils and other components, such as disclosed for example in U.S. Pat. Nos. 8,377,554; 8,093,161; and 6,821,301. In some configurations, a spin finish may include various types of silicone oils, such as for example, polydimethylsiloxane. In some configurations, a spin finish may include various types of mineral oils, including hydrogenated paraffinic and napthenic oils. In some configurations, the molecular weight of an oil may be adjusted to optimize adhesion properties of the elastic strands depending on the process configuration in which the elastic strands may be used. In some configurations, a spin finish may include various types of fatty amides, erucamide, behenamide, and oleamide. It is also to be appreciated that the amount of spin finish applied to elastic strands may be optimized depending on the process configuration in which the elastic strands may be used. For example, in process configurations wherein elastic strands have limited contact or do not contact downstream handling equipment, such as idlers, the amount of spin finish may be selected to help prevent the elastics strands from adhering to themselves and/or each other while wound on a beam without regard to whether elastic strands would adhere to downstream handling equipment. As such, it is to be appreciated that the elastic strands herein may include various amounts of spin finish that may be expressed in various ways. For example, a quantity of 10 grams of spin finish per 1 kilogram of elastic strand may be expressed as 1% spin finish. In some configurations, an elastic strand may include about 0.1% spin finish. In some configurations, a strand may include from about 0.01% to about 10% spin finish, specifically reciting all 0.01% increments within the above-recited range and all ranges formed therein or thereby. It is also to be appreciated that the methods and apparatuses herein may also be configured to remove some or all the spin finish from the elastic strands 318. Examples of spin finish removal processes and apparatuses are disclosed in U.S. Provisional Patent Application No. 62/483,965, which is incorporated by reference herein.

This application claims the benefit of U.S. Provisional Application No. 62/436,589, filed on Dec. 20, 2016; 62/483,965, filed on Apr. 11, 2017; 62/553,538, filed on Sep. 1, 2017; 62/553,149, filed on Sep. 1, 2017; 62/553,171, filed on Sep. 1, 2017; and 62/581,278, filed on Nov. 3, 2017, the entireties of which are all incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an elastomeric laminate, the method comprising steps of:

providing first spools, each first spool comprising an outer circumferential surface defined by an elastic strand wound onto a core;

positioning the outer circumferential surface of each first spool in rolling contact with a first roll;

unwinding elastic strands from the first spools in a machine direction at a speed S2, wherein the elastic strands from the first spools are separated from each other in the cross direction by advancing the elastic strands from between each first spool and the first roll;

stretching the elastic strands from the first spools, wherein the elastic strands from the first spools comprise first elastic strands and second elastic strands;

bonding the stretched first elastic strands and stretched second elastic strands from the first spools with and between a first substrate and a second substrate to form an elastomeric laminate, wherein the elastomeric laminate comprises a first region having a first stretch characteristic defined by the first elastic strands and a second region having a second stretch characteristic defined by the second elastic strands, wherein the first stretch characteristic is different from the second stretch characteristic;

rotating a first roller about a first axis of rotation extending in a cross direction, the first roller comprising an outer circumferential surface comprising a surface speed S1;

rotating a second roller about a second axis of rotation extending in the cross direction, the second roller comprising an outer circumferential surface comprising a surface speed S1, wherein S2 is less than S1, and wherein the first roller and the second roller rotate in opposite directions, and wherein the first roller is adjacent the second roller to define a nip between the first roller and the second roller;

advancing the first substrate and the second substrate through the nip;

stretching the elastic strands from the first spools in the machine direction by advancing the elastic strands from the first spools through the nip and between the first substrate and the second substrate.

2. The method of claim 1, further comprising a step of rotating the first spools and the first roll in opposite directions.

3. The method of claim 2, further comprising a step of rotating the first spools by rotating the first roll.

4. The method of claim 1, wherein the elastic strands from the first spools comprise a decitex from about 10 to about 500.

5. The method of claim 1, further comprising a step of separating the elastic strands from the first spools from each other by 0.5 mm to 4 mm.

6. The method of claim 1, further comprising a step of changing distances between the elastic strands from the first spools subsequent to unwinding from the first spools.

7. The method of claim 1, wherein the first elastic strands are separated from each other by a first distance in a cross direction, wherein the second elastic strands are separated from each other by a second distance in a cross direction, and wherein the first distance is different from the second distance.

8. The method of claim 1, wherein the first elastic strands comprise a first decitex and the second elastic strands comprise a second decitex, wherein the first decitex and the second decitex are not equal.

\* \* \* \* \*